United States Patent
Machold et al.

(10) Patent No.: US 7,658,755 B2
(45) Date of Patent: Feb. 9, 2010

(54) DISPOSABLE CASSETTE FOR INTRAVASCULAR HEAT EXCHANGE CATHETER

(75) Inventors: Timothy R. Machold, Moss Beach, CA (US); Nicole Denise Bloom, San Francisco, CA (US); Alex T. Roth, Redwood City, CA (US); Dave J. Scott, Santa Clara, CA (US); Jose Alejandro, San Jose, CA (US); Edward A. Oliver, Los Gatos, CA (US)

(73) Assignee: Radiant Medical, Inc., Sunnyvale, CA (US)

(*) Notice: Subject to any disclaimer, the term of this patent is extended or adjusted under 35 U.S.C. 154(b) by 639 days.

(21) Appl. No.: 10/627,487

(22) Filed: Jul. 25, 2003

(65) Prior Publication Data

US 2005/0075705 A1   Apr. 7, 2005

Related U.S. Application Data

(60) Division of application No. 09/563,946, filed on May 2, 2000, now Pat. No. 6,673,098, which is a continuation-in-part of application No. 09/138,830, filed on Aug. 24, 1998, now Pat. No. 6,620,188.

(60) Provisional application No. 60/185,561, filed on Feb. 28, 2000.

(51) Int. Cl.
*A61F 7/00* (2006.01)
(52) U.S. Cl. ............................. 607/96; 607/113; 607/114
(58) Field of Classification Search ........................ None
See application file for complete search history.

(56) References Cited

U.S. PATENT DOCUMENTS

| 3,369,549 | A | | 2/1968 | Armao |
| 4,111,209 | A | | 9/1978 | Wolvek et al. |
| 4,459,468 | A | | 7/1984 | Bailey |
| 4,767,289 | A | | 8/1988 | Parrott et al. |
| 4,800,823 | A | * | 1/1989 | Hyatt ......................... 109/24 |

(Continued)

FOREIGN PATENT DOCUMENTS

AU        730835        3/2001

(Continued)

OTHER PUBLICATIONS

European Patent Office Search Report dated Jul. 20, 2007.

*Primary Examiner*—Robert L Nasser
(74) *Attorney, Agent, or Firm*—John K. Fitzgerald; Fulwider Patton LLP

(57) ABSTRACT

A heat exchange fluid supply system for supplying a heat exchange fluid to an intravascular heat exchange catheter includes a disposable cassette having a bulkhead and an external heat exchanger, and which is configured to operate in combination with a reusable master control unit. The bulkhead includes a reservoir section and a pump section. The reservoir section is provided with a means to monitor the amount of heat exchange fluid that is in the system. The bulkhead provides the mechanism for priming the system with heat exchange fluid from an external source and for circulating fluid to the catheter in a closed circuit. The pump section is configured to allow for pumping of heat exchange fluid at a constant pressure.

5 Claims, 21 Drawing Sheets

U.S. PATENT DOCUMENTS

| | | | |
|---|---|---|---|
| 4,919,134 A | 4/1990 | Streeter |
| 4,941,475 A | 7/1990 | Williams et al. |
| 4,960,103 A | 10/1990 | Urso |
| 4,962,761 A | 10/1990 | Golden |
| 5,097,829 A | 3/1992 | Quisenberry |
| 5,174,285 A | 12/1992 | Fontenot |
| 5,211,631 A | 5/1993 | Sheaff |
| 5,330,519 A | 7/1994 | Mason et al. |
| 5,334,181 A | 8/1994 | Rubinsky et al. |
| 5,342,182 A | 8/1994 | Montoya et al. |
| 5,344,436 A | 9/1994 | Fontenot et al. |
| 5,387,088 A | 2/1995 | Knapp et al. |
| 5,476,368 A | 12/1995 | Rabenau et al. |
| 5,486,208 A | 1/1996 | Ginsburg |
| 5,514,094 A | 5/1996 | Anello et al. |
| 5,563,584 A | 10/1996 | Rader et al. |
| 5,624,392 A | 4/1997 | Saab |
| 5,645,531 A | 7/1997 | Thompson et al. |
| 5,716,386 A | 2/1998 | Ward et al. |
| 5,733,319 A | 3/1998 | Neilson et al. |
| 5,837,003 A | 11/1998 | Ginsburg |
| 5,871,526 A | 2/1999 | Gibbs et al. |
| 5,879,329 A | 3/1999 | Ginsburg |
| 5,895,418 A | 4/1999 | Saringer |
| 5,957,963 A | 9/1999 | Dobak, III |
| 5,972,013 A | 10/1999 | Schmidt |
| 5,980,561 A | 11/1999 | Kolen et al. |
| 5,989,238 A | 11/1999 | Ginsburg |
| 6,019,783 A | 2/2000 | Philips et al. |
| 6,051,019 A | 4/2000 | Dobak, III |
| 6,096,068 A | 8/2000 | Dobak, III et al. |
| 6,146,411 A * | 11/2000 | Noda et al. ............... 607/105 |
| 6,149,676 A | 11/2000 | Ginsburg |
| 6,206,004 B1 | 3/2001 | Schmidt et al. |
| 6,224,624 B1 | 5/2001 | Lasheras et al. |
| 6,231,595 B1 | 5/2001 | Dobak, III |
| 6,235,048 B1 | 5/2001 | Dobak, III |
| 6,251,129 B1 | 6/2001 | Dobak, III et al. |
| 6,254,626 B1 | 7/2001 | Dobak, III et al. |
| 6,261,312 B1 | 7/2001 | Dobak, III et al. |
| 6,383,158 B1 * | 5/2002 | Utterberg et al. ........... 604/4.01 |
| 6,396,583 B1 | 5/2002 | Clare |
| 6,620,188 B1 * | 9/2003 | Ginsburg et al. ........... 607/106 |

FOREIGN PATENT DOCUMENTS

| | | |
|---|---|---|
| AU | 756115 | 1/2003 |
| AU | 772661 | 5/2004 |
| GB | 2312736 | 11/1997 |
| WO | 94/17842 A1 | 8/1994 |
| WO | 97/39707 A1 | 10/1997 |
| WO | WO 00/09054 | 2/2000 |
| WO | WO 00/10494 | 3/2000 |
| WO | 00/38601 A1 | 7/2000 |
| WO | WO 00/48670 | 8/2000 |
| WO | WO 00/66053 | 11/2000 |

* cited by examiner

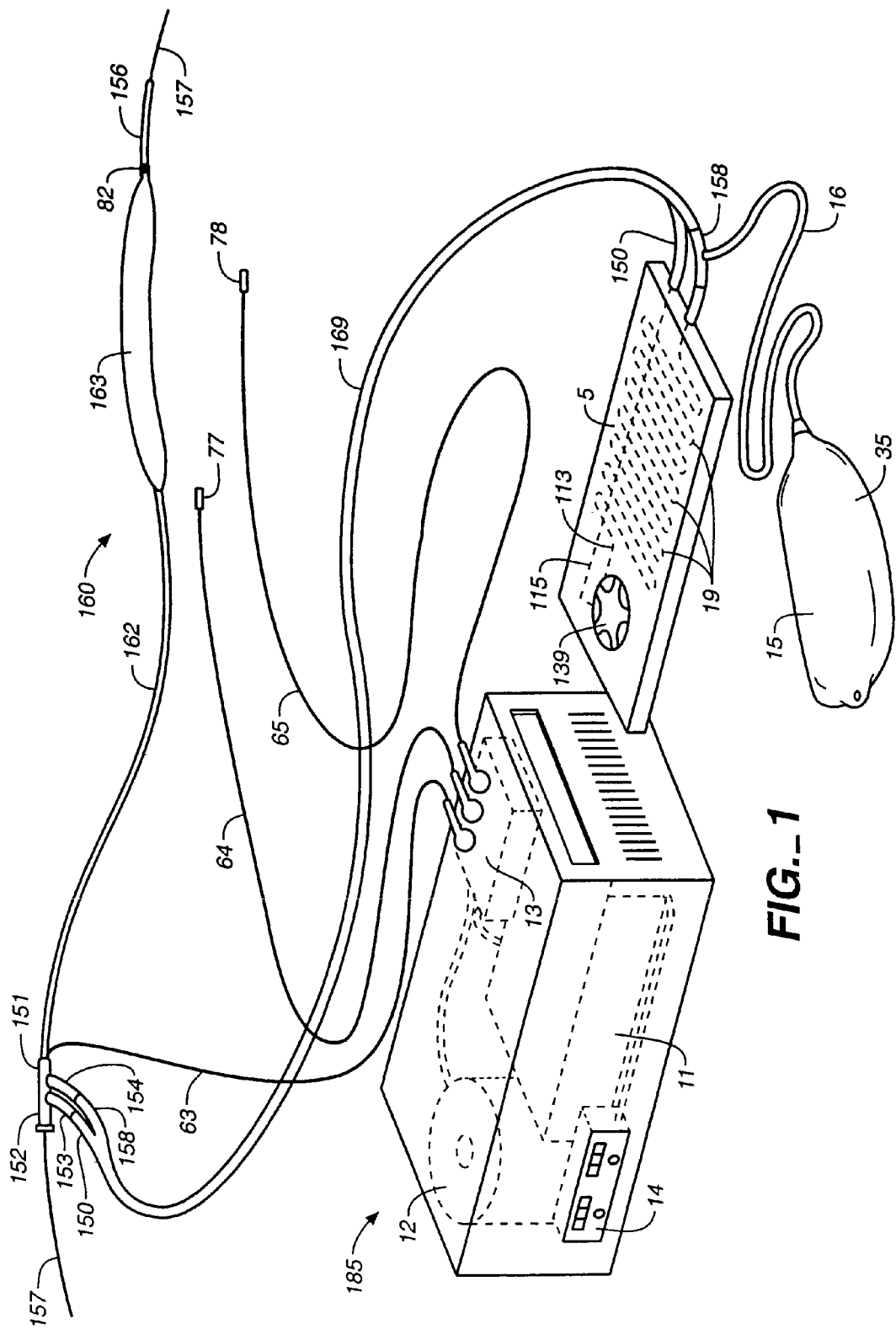
FIG._1

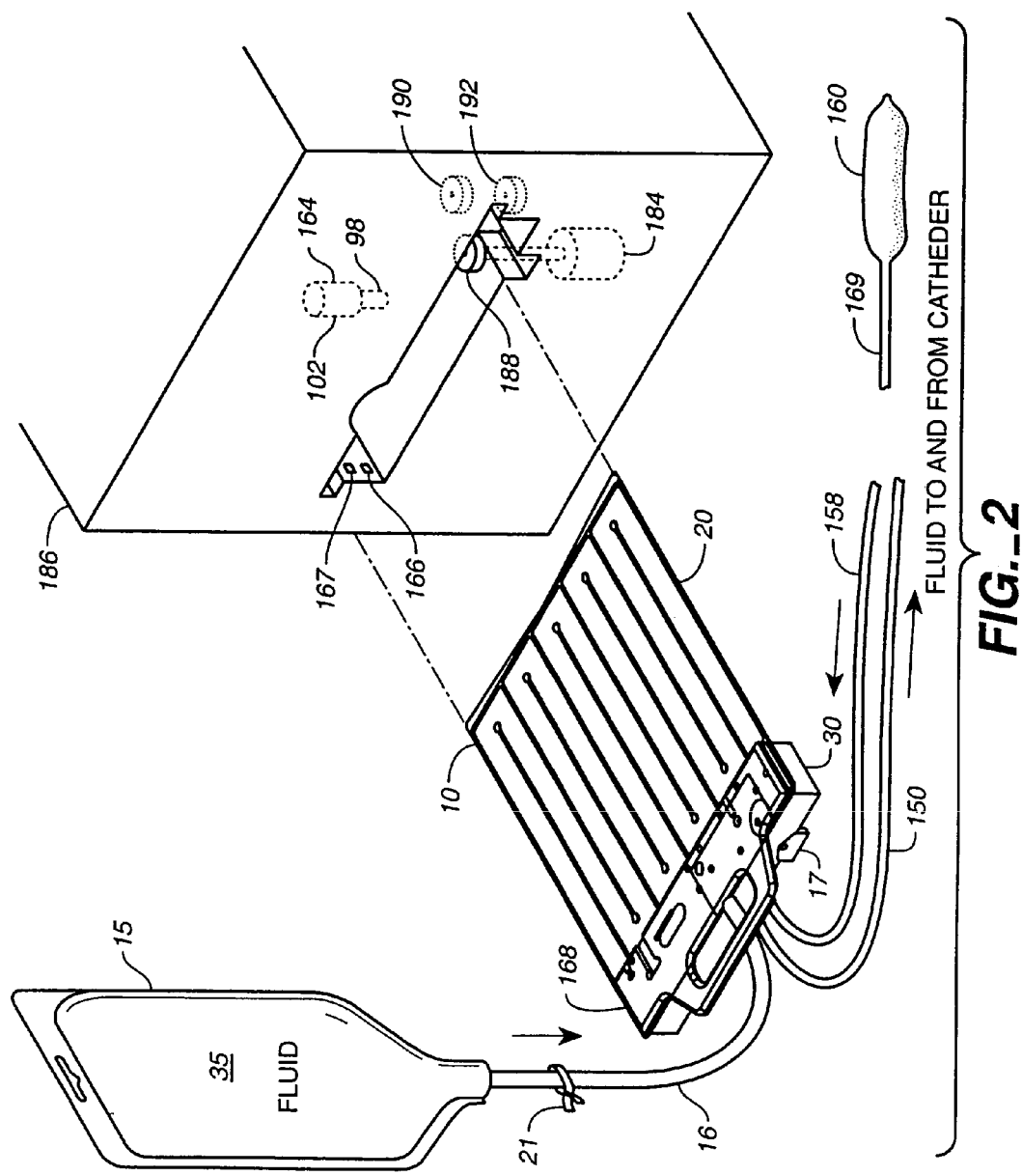
FIG._2

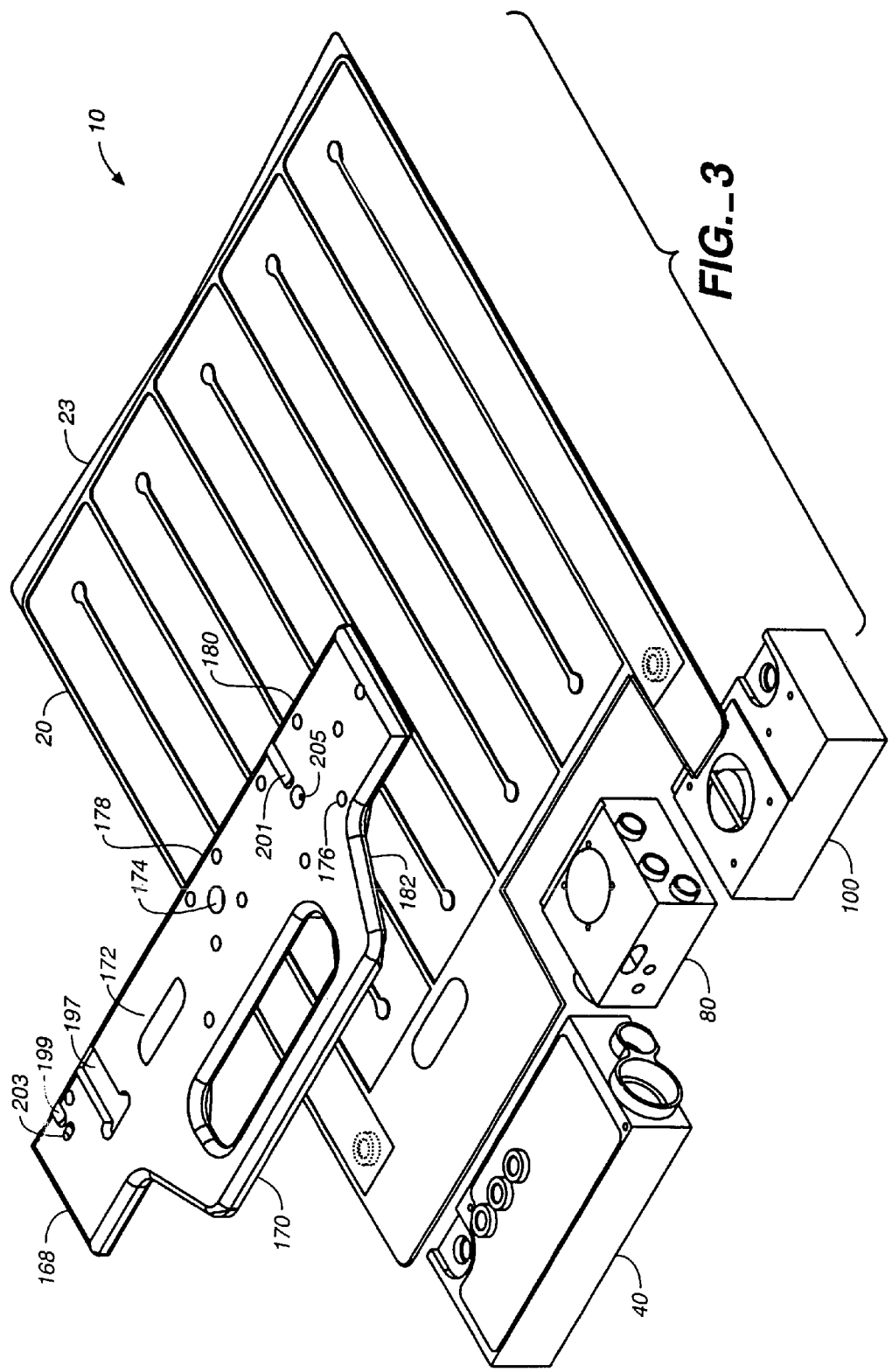
FIG._3

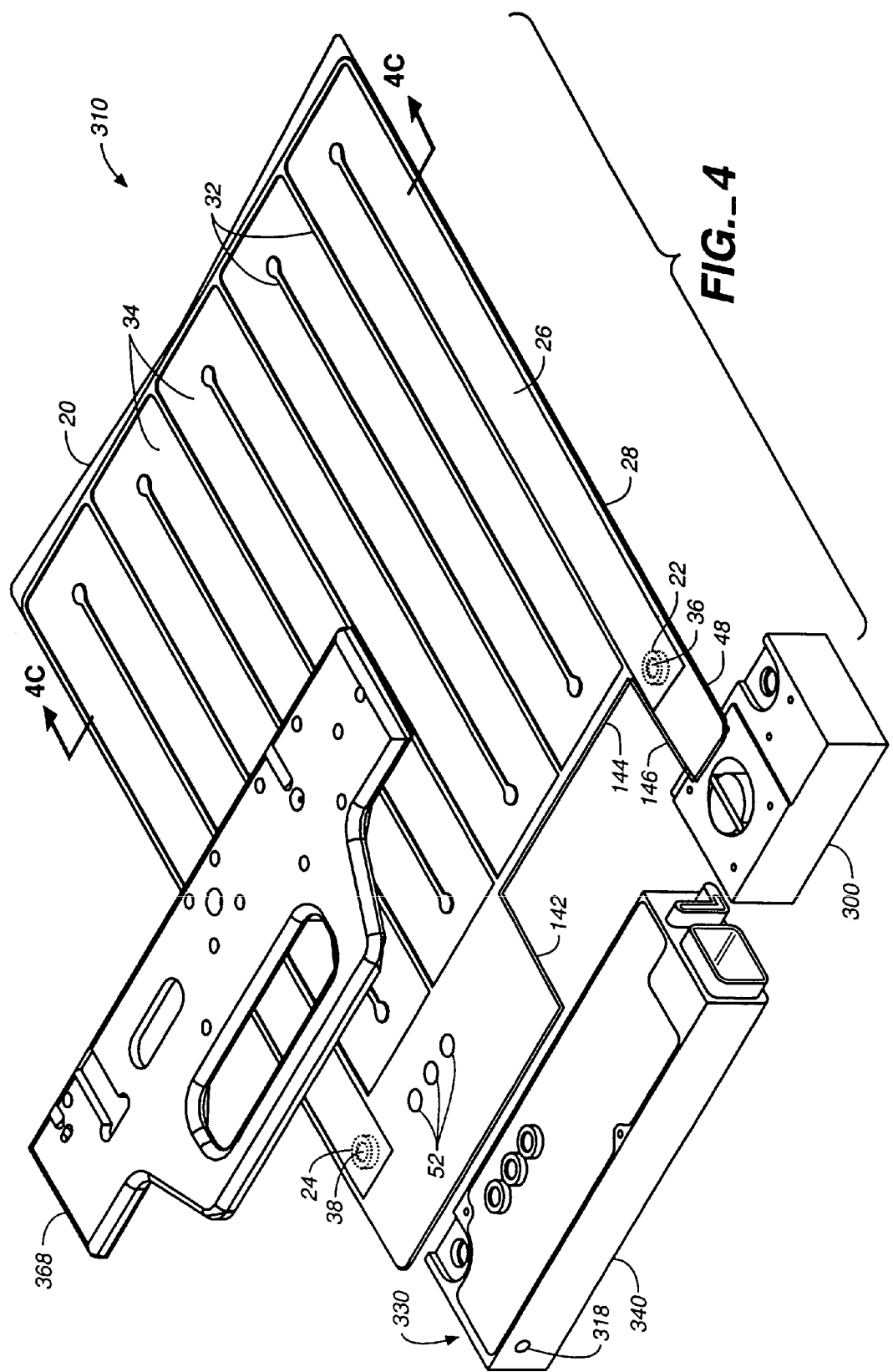
FIG._4

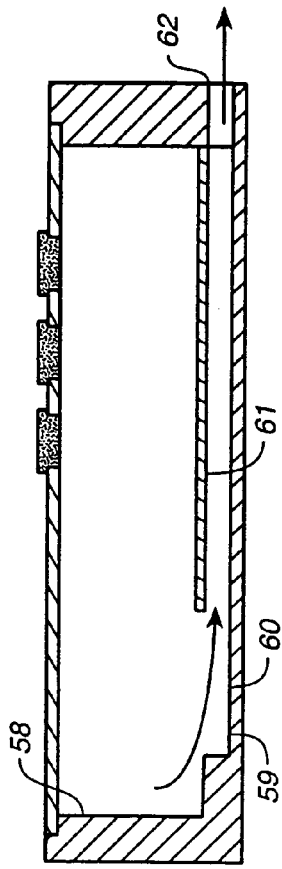
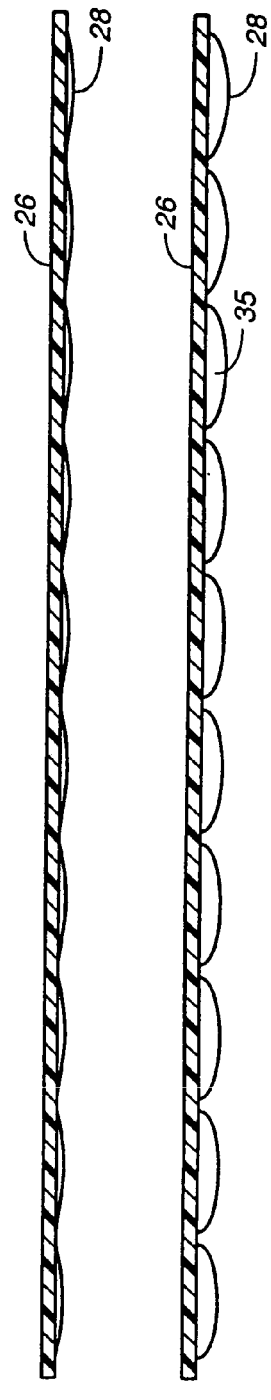
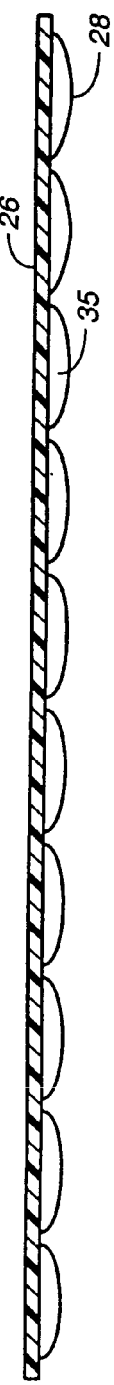
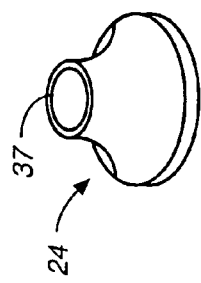
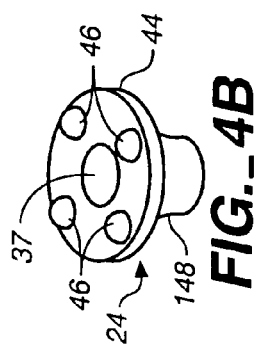
FIG._5B
FIG._4A
FIG._4B
FIG._4C
FIG._4D

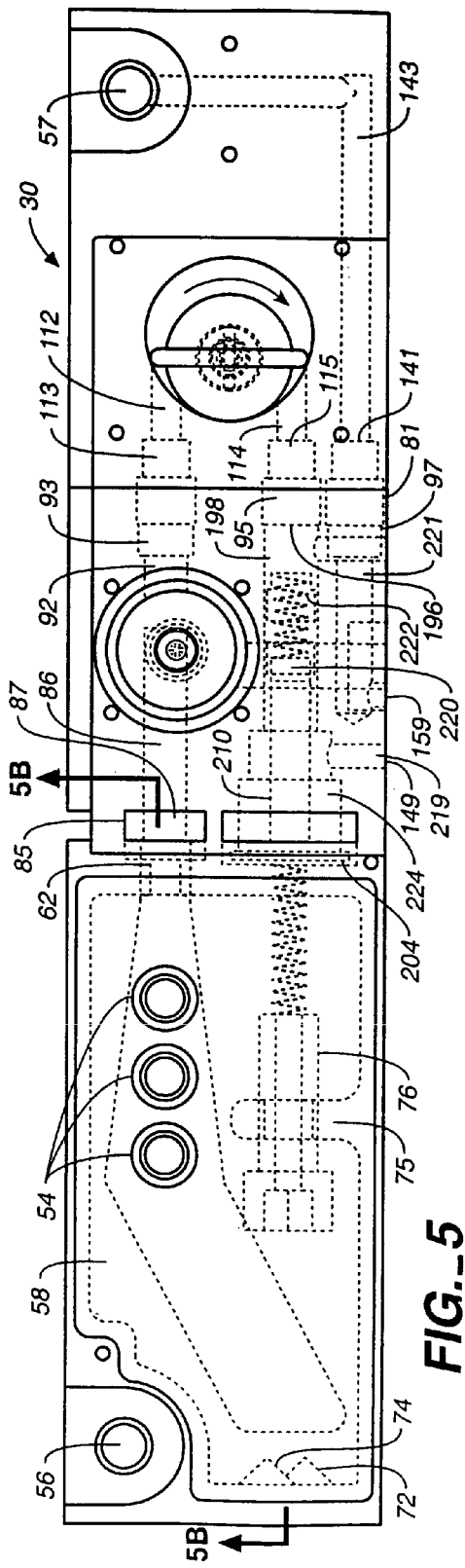
FIG._5
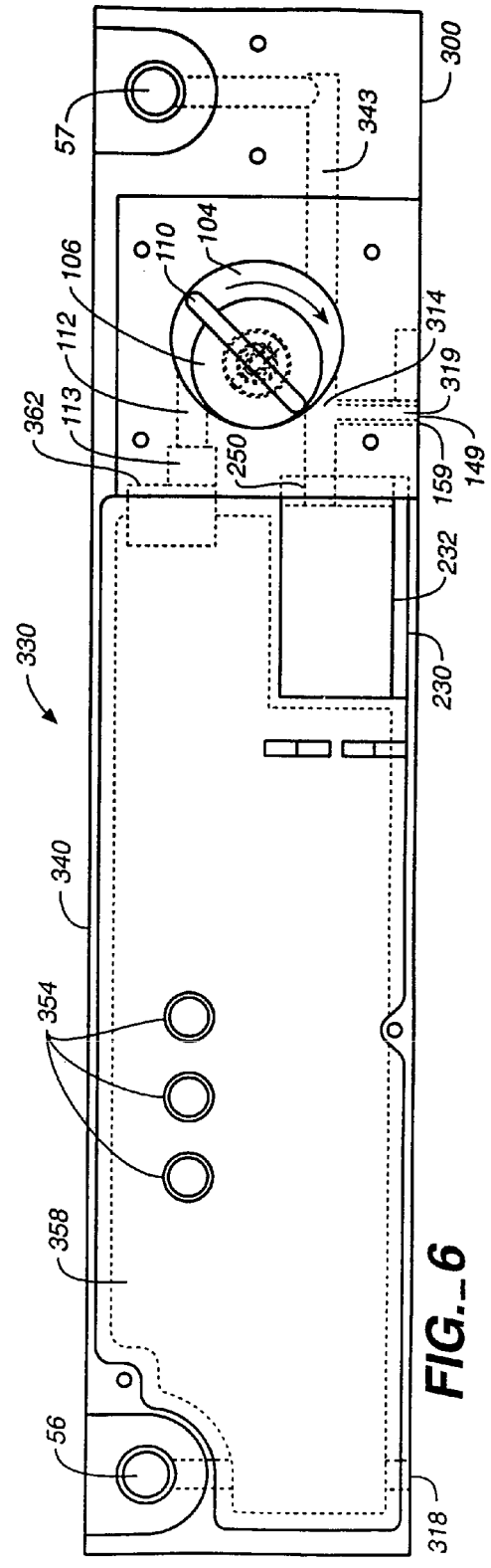
FIG._6

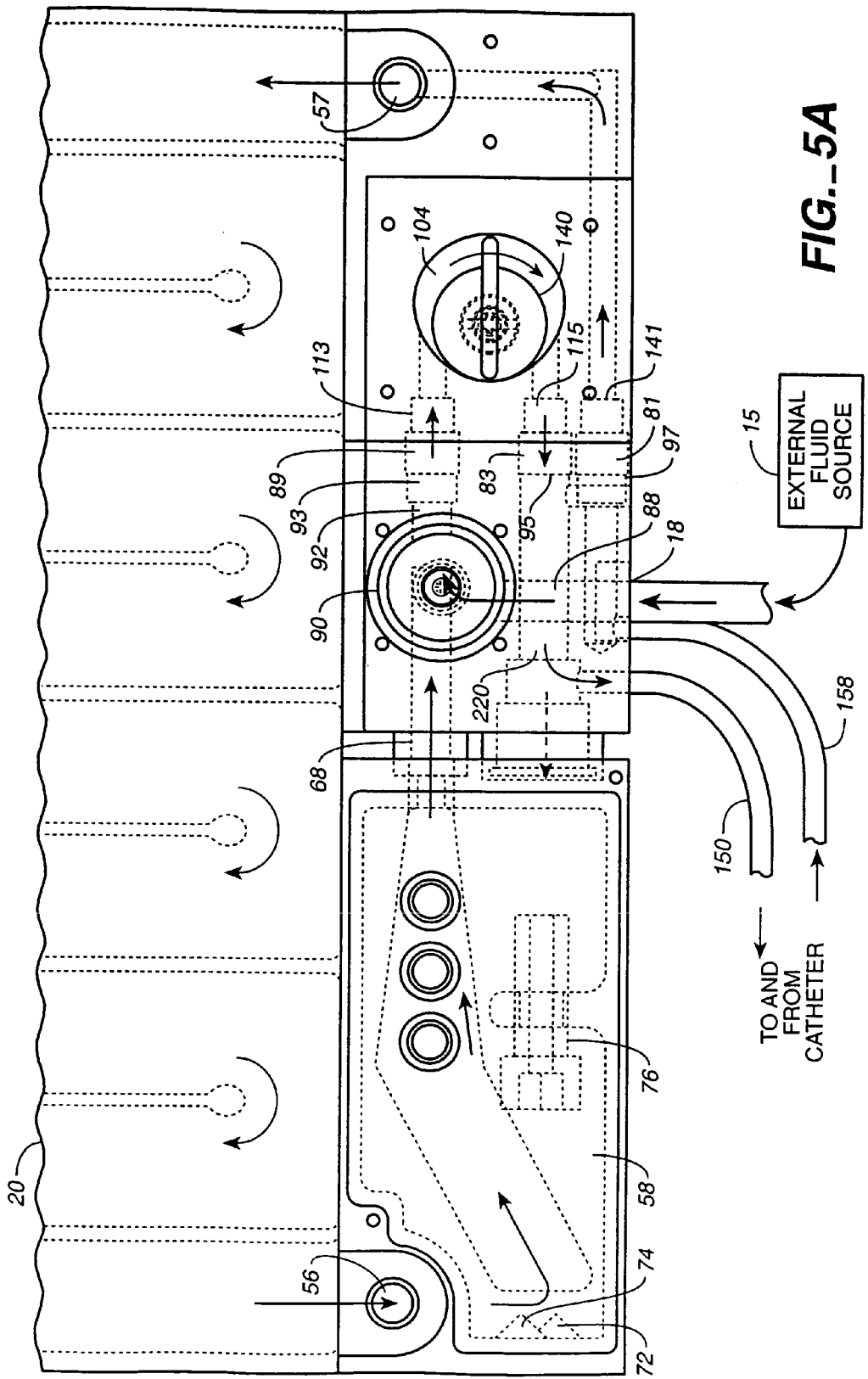
FIG._5A

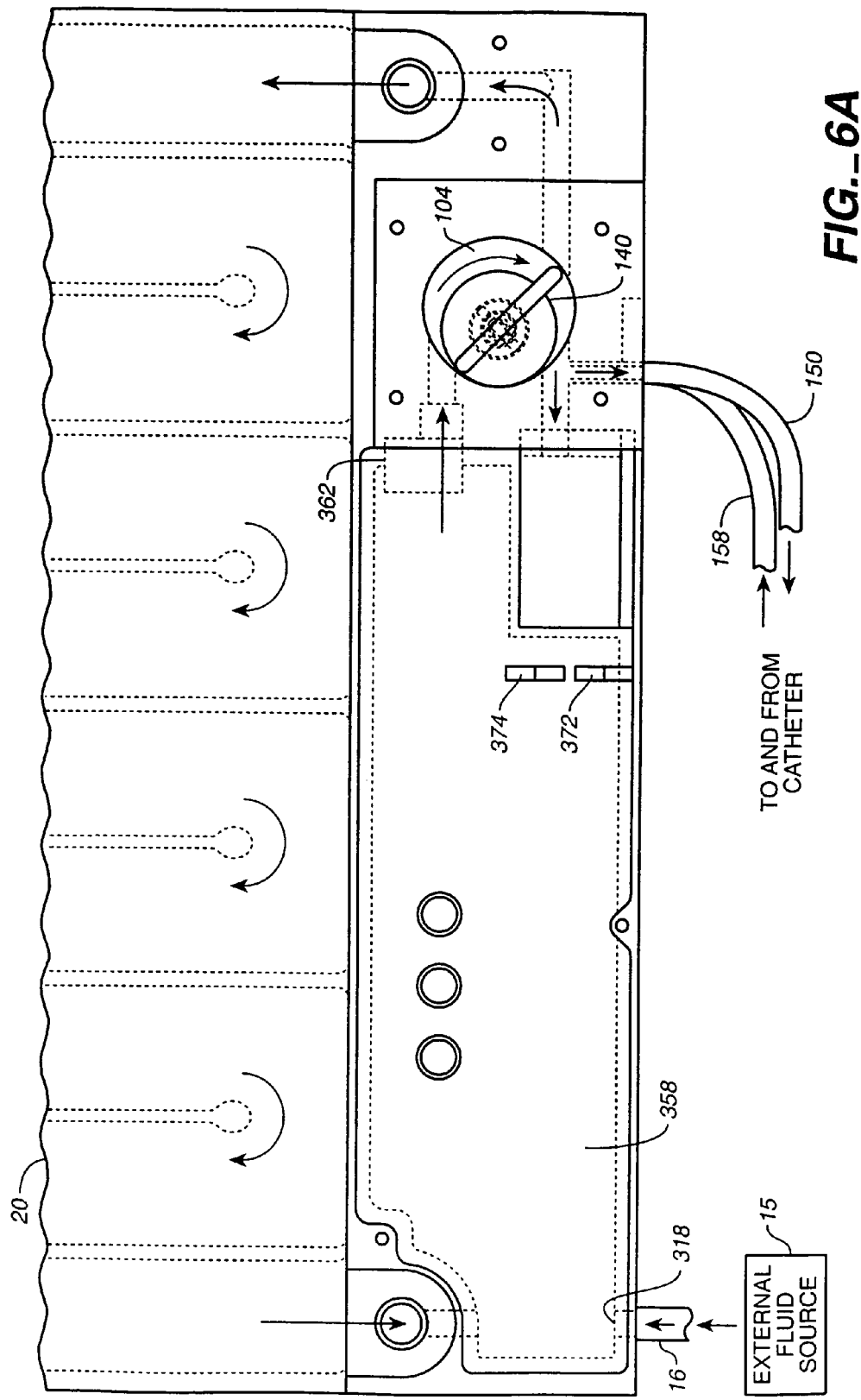
FIG._6A

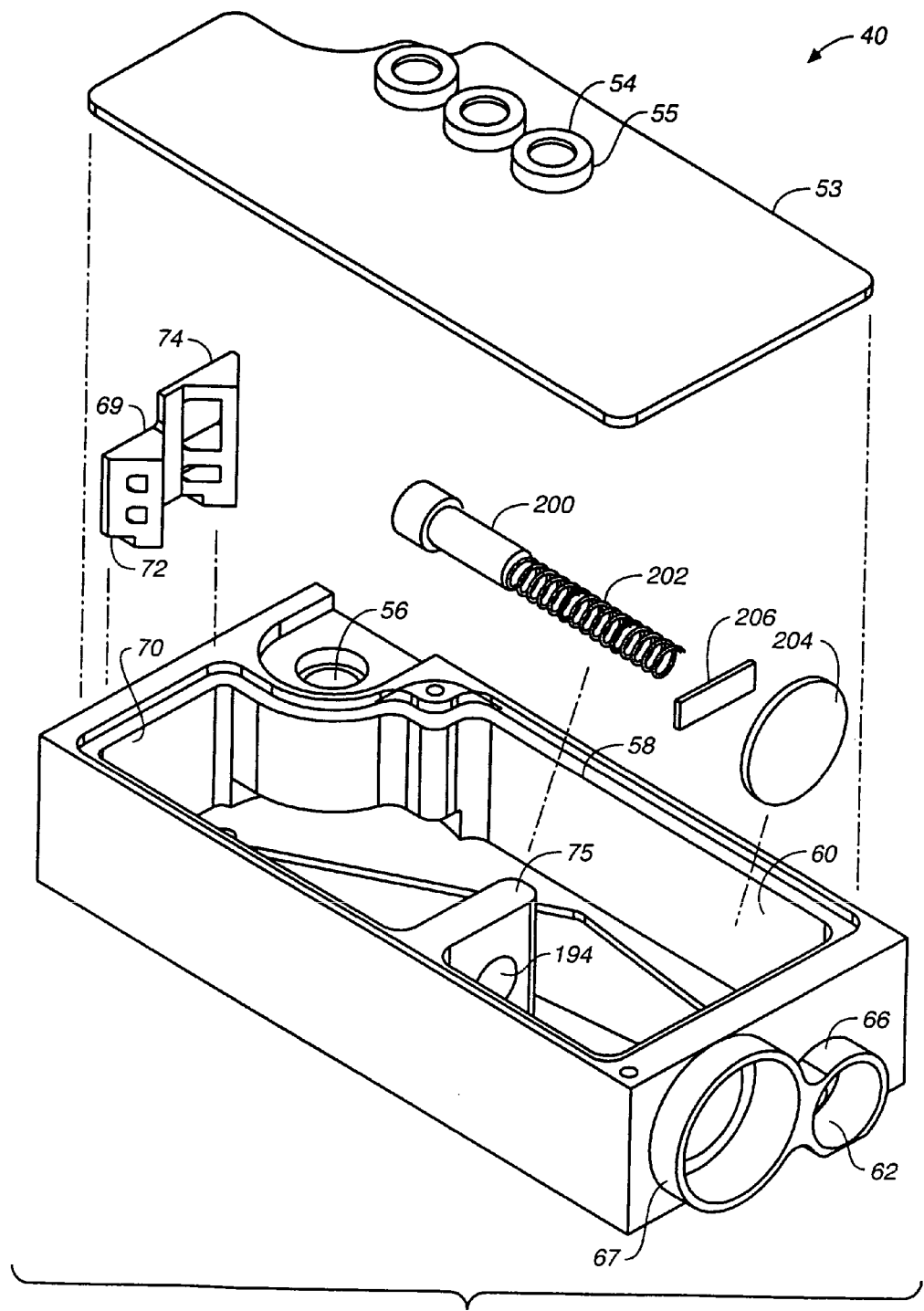
FIG._7

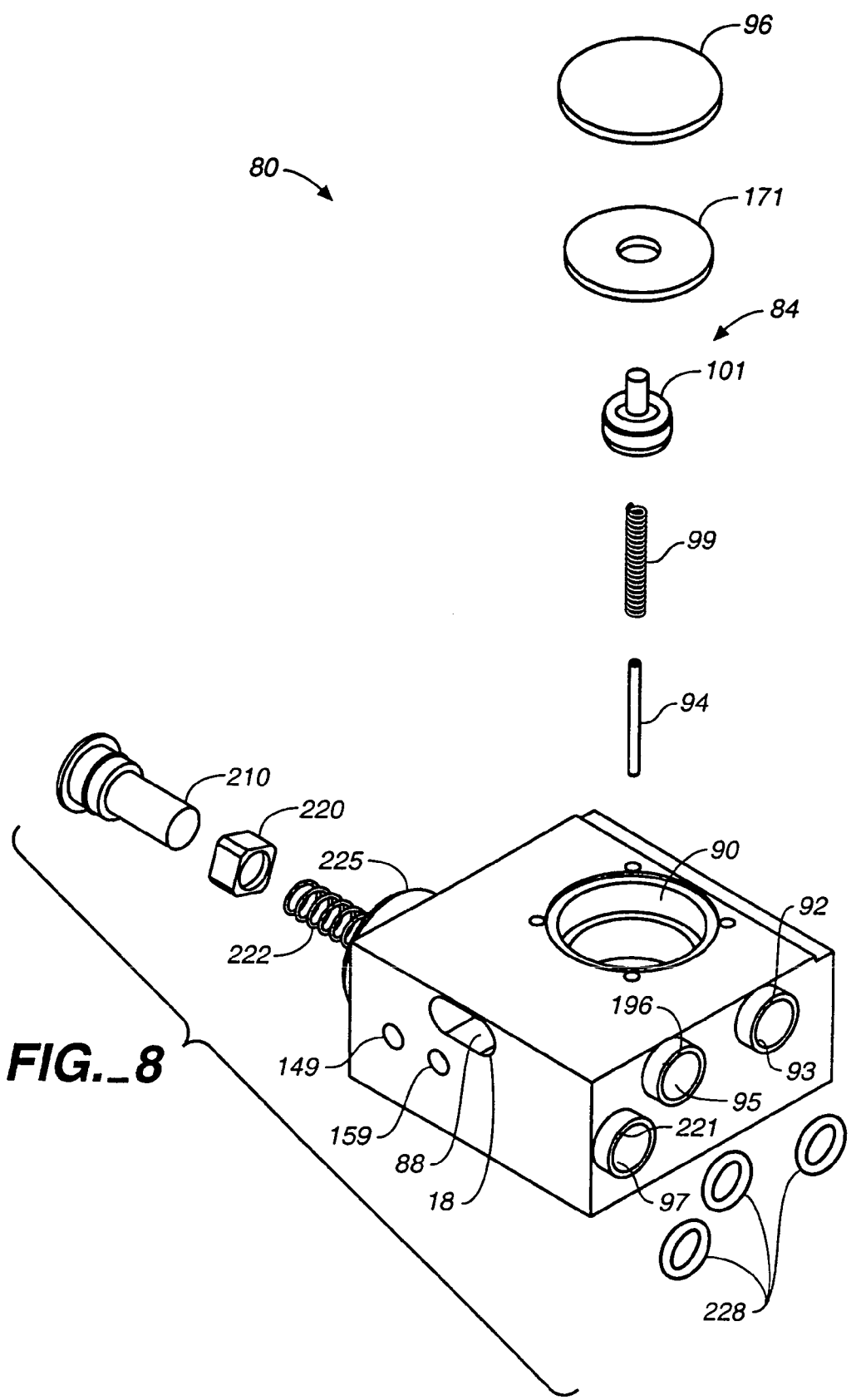
FIG._8

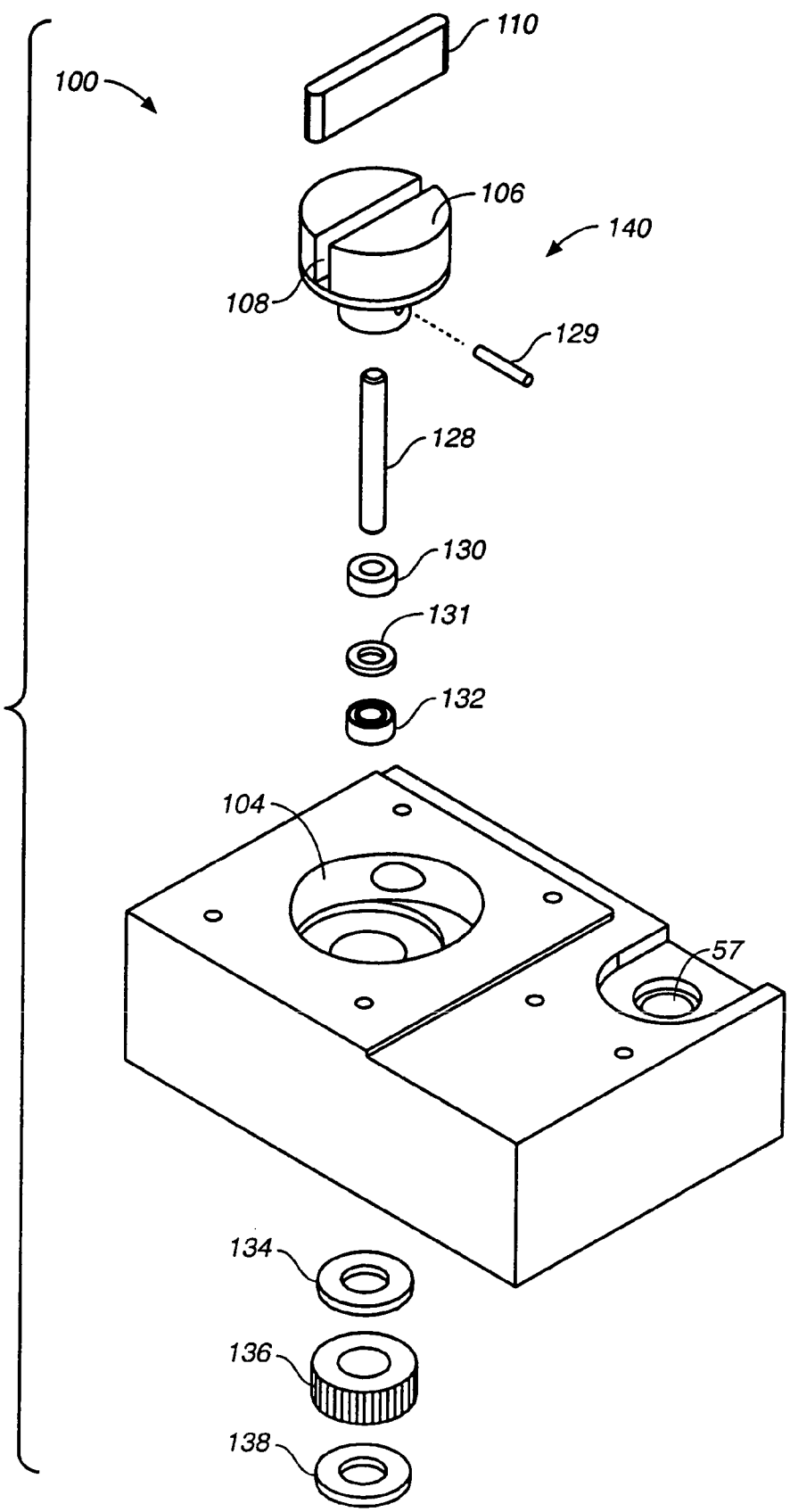

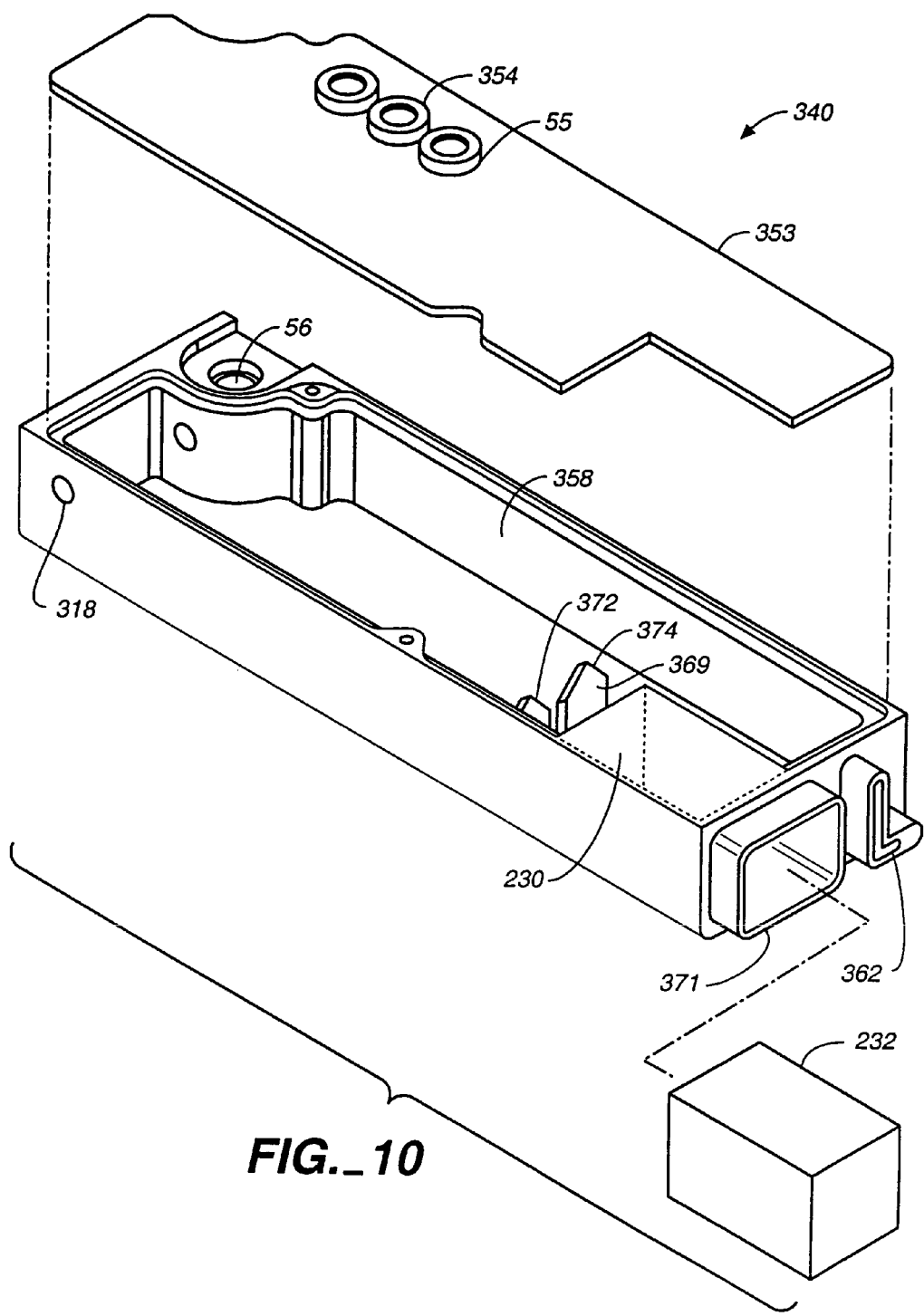
FIG._10

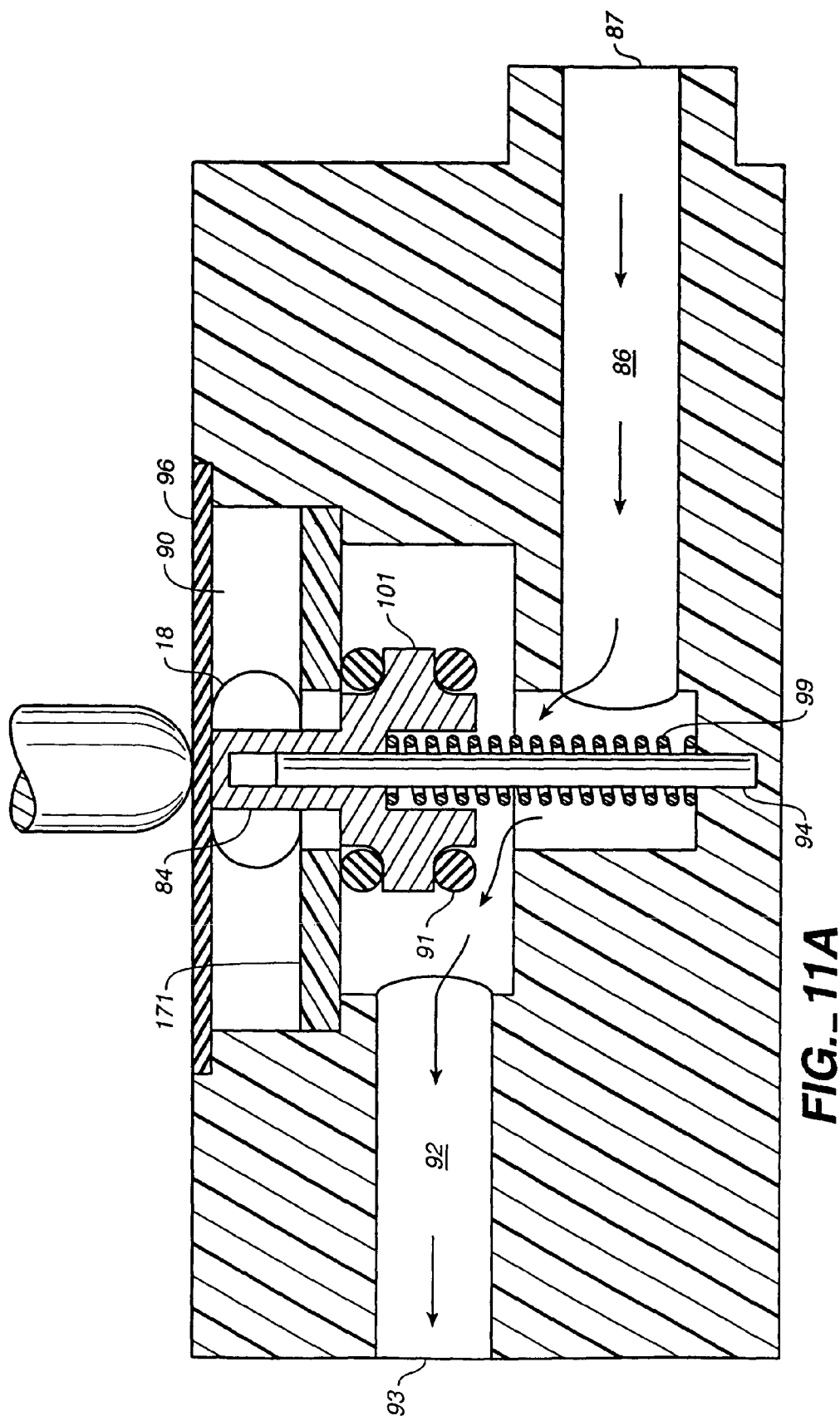
FIG._11A

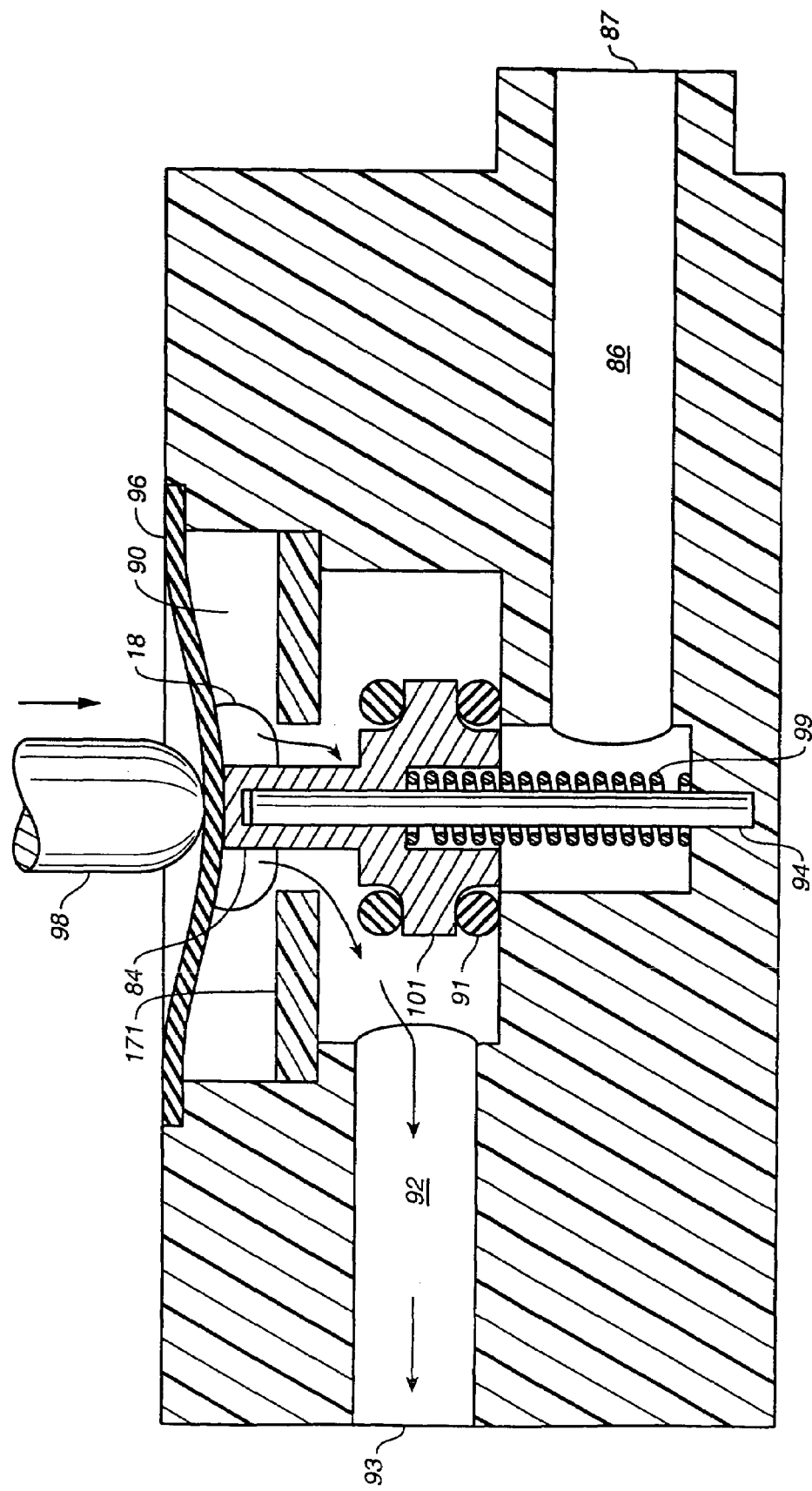
FIG._11B

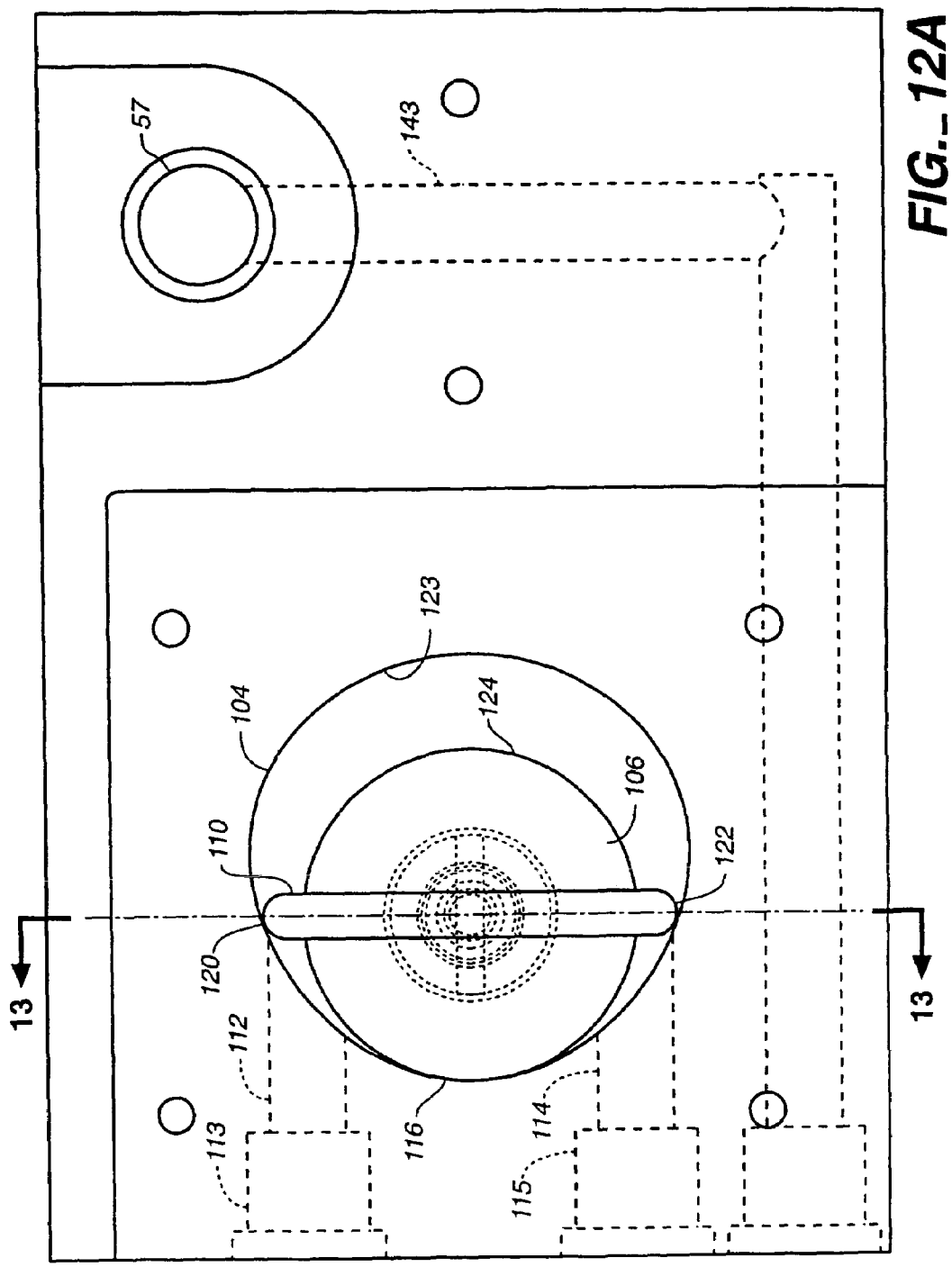

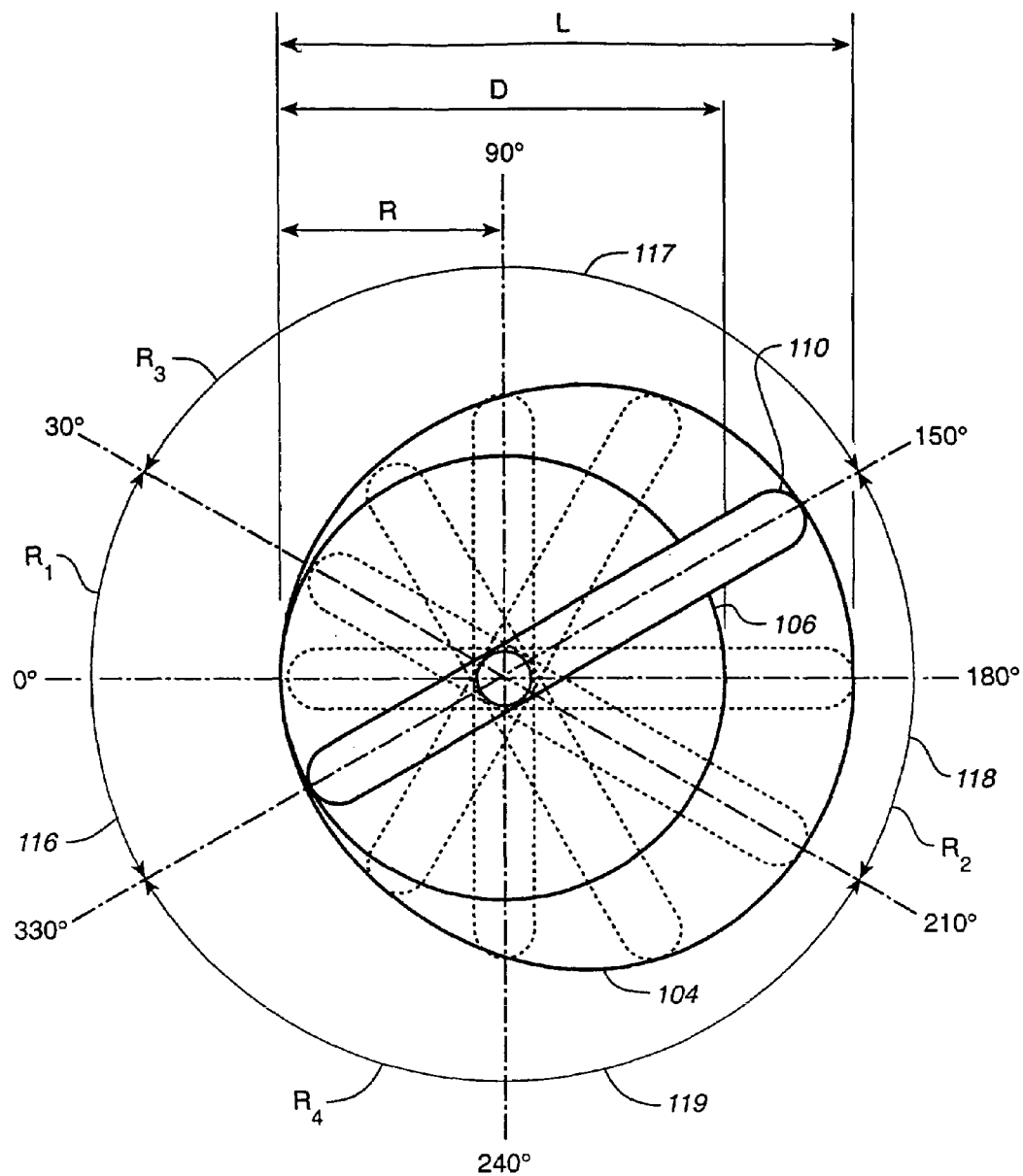
FIG._12B

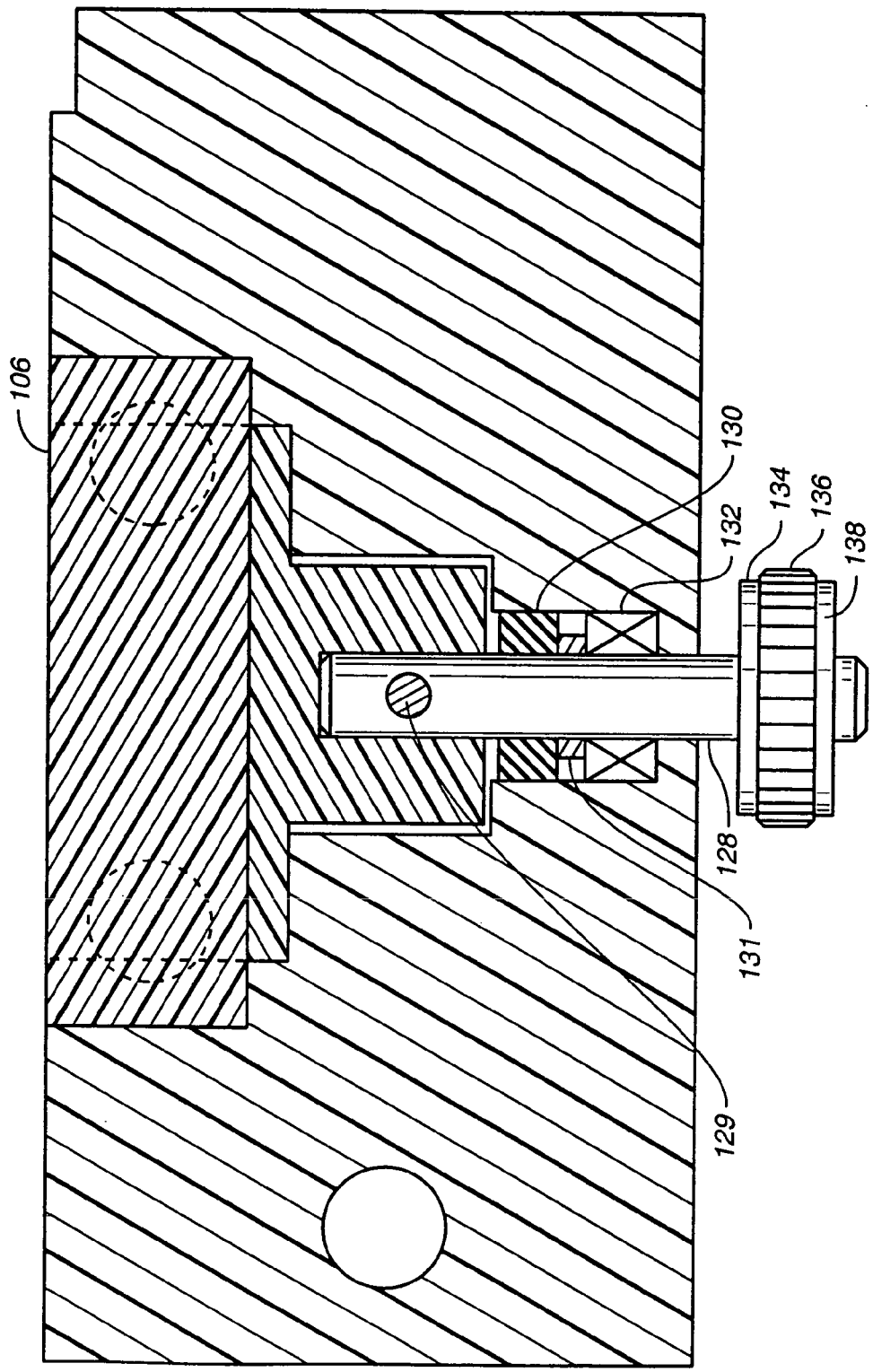
FIG._13

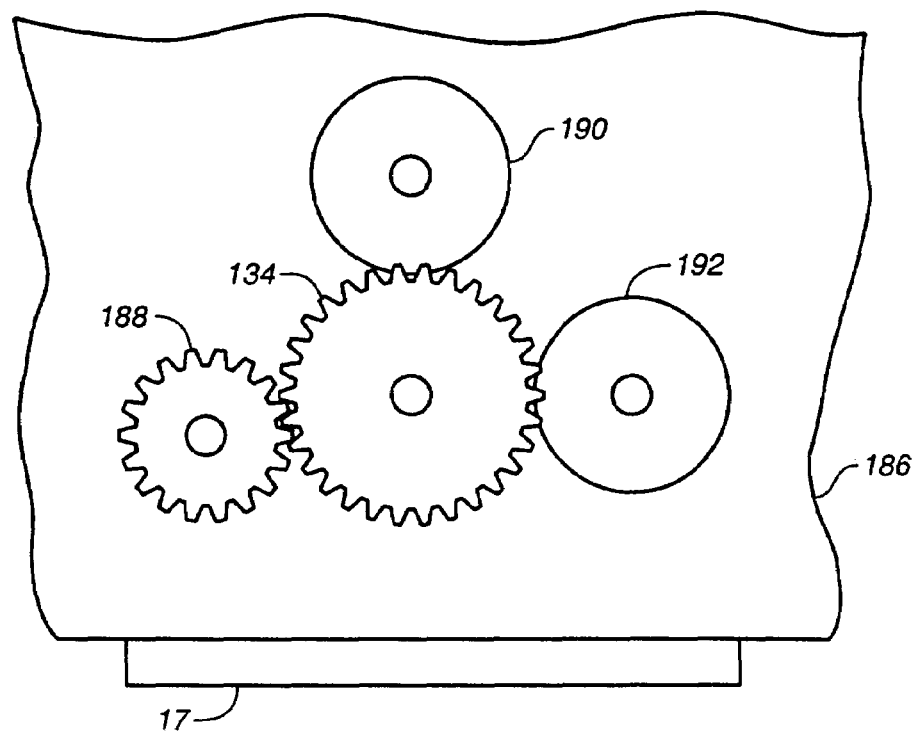
FIG._14
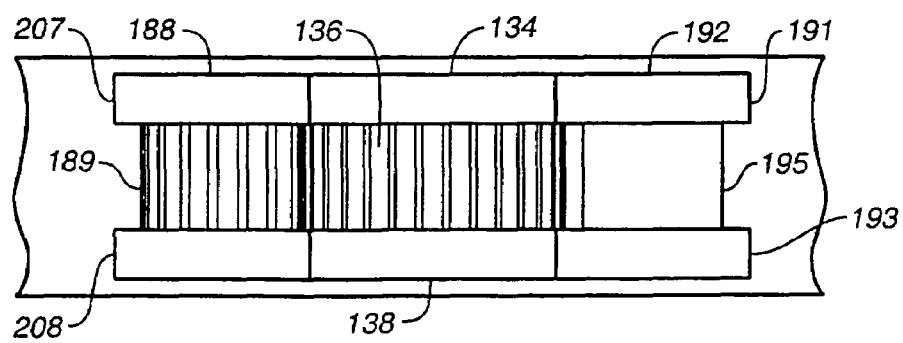
FIG._15

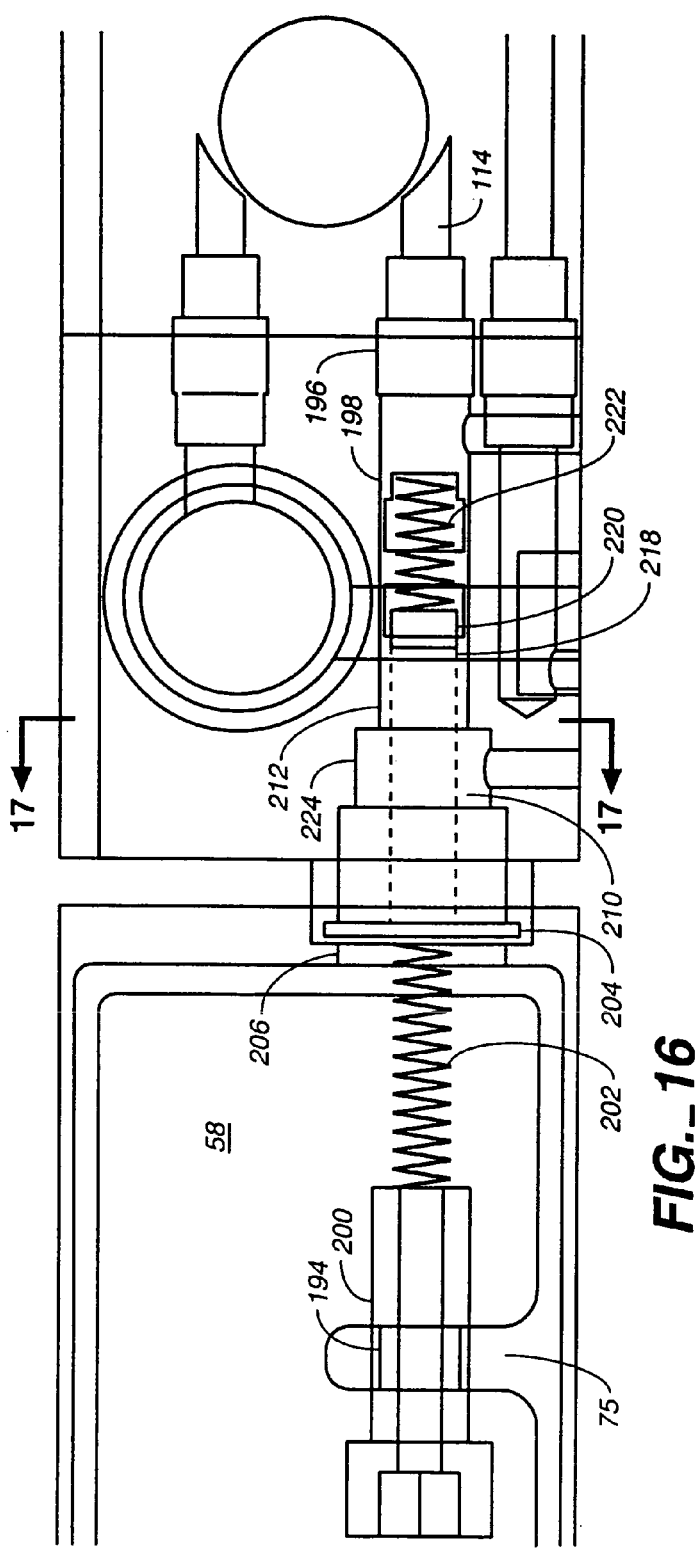
FIG._16
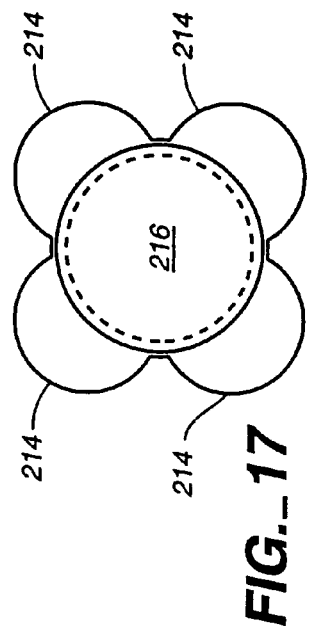
FIG._17

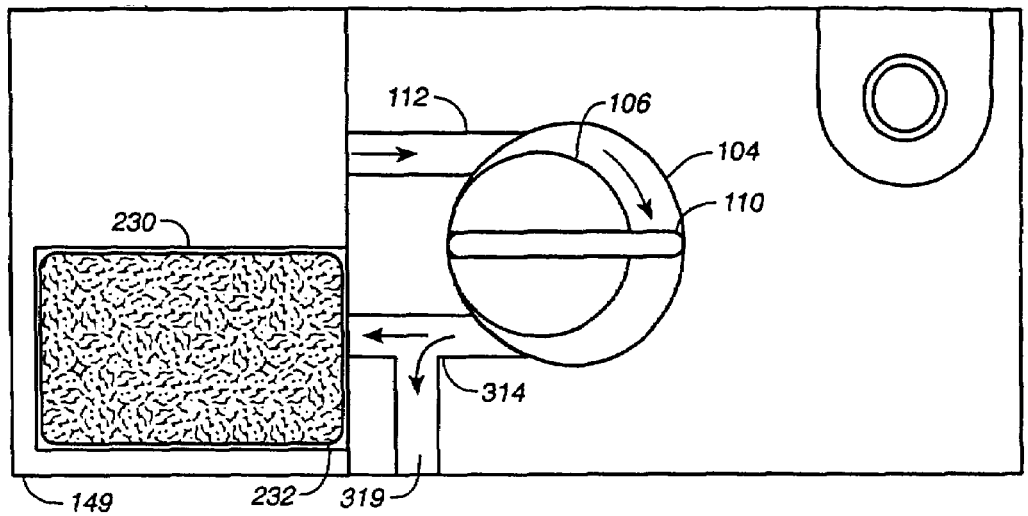
FIG._18
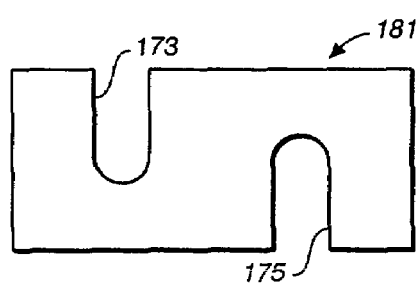
FIG._20A
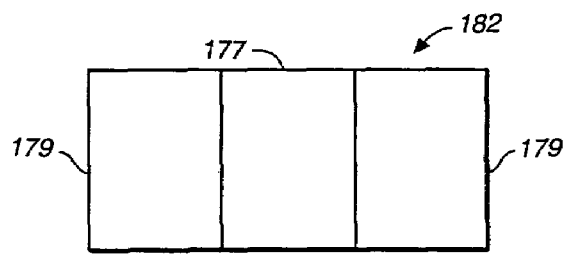
FIG._20B
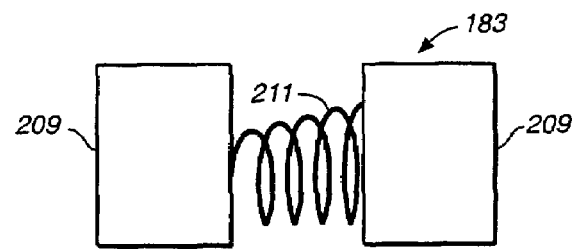
FIG._20C

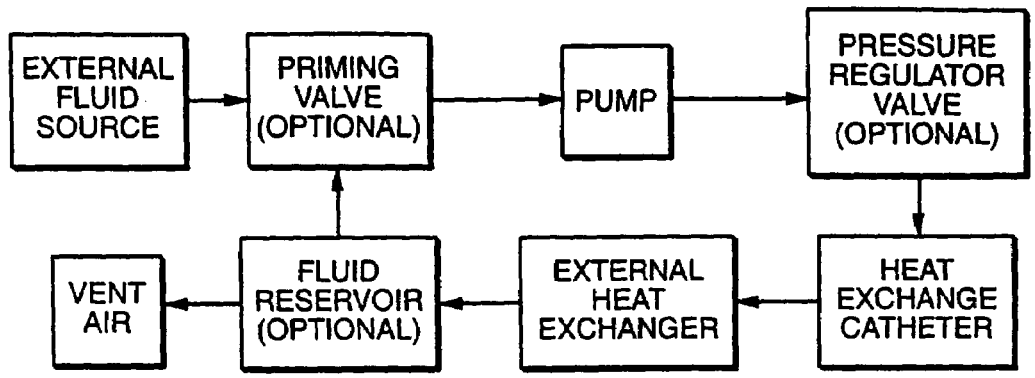
FIG._19A
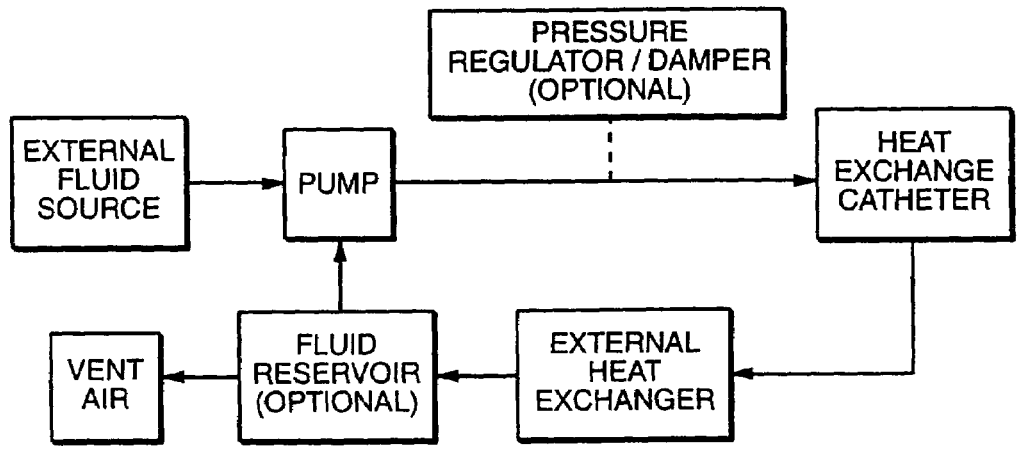
FIG._19B
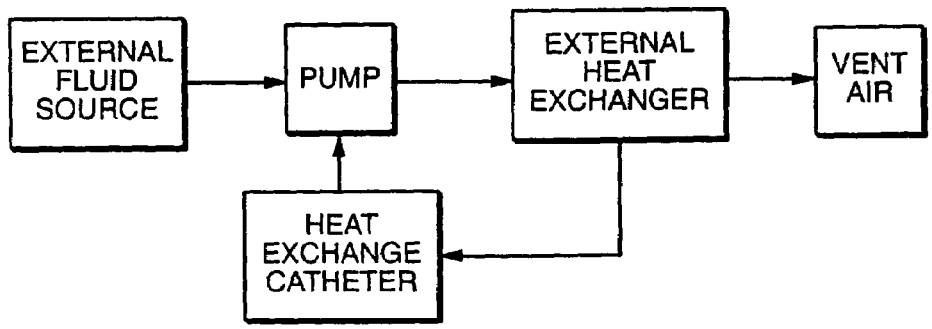
FIG._19C

DISPOSABLE CASSETTE FOR INTRAVASCULAR HEAT EXCHANGE CATHETER

CROSS REFERENCE TO RELATED APPLICATIONS

This application is a divisional application of U.S. Ser. No. 09/563,946 filed May 2, 2000, now U.S. Pat. No. 6,673,098 which is a continuation-in-part of U.S. Ser. No. 09/138,830, filed Aug. 24, 1998, now U.S. Pat. No. 6,620,188 which claimed priority of 60/185,561, Feb. 28, 2000.

TECHNICAL FIELD

The present invention is directed to a fluid supply and fluid handling mechanism for an intravascular heat exchanger, and more particularly to a disposable cassette with a pump head and an external heat exchanger for use as a system to provide hot or cold heat transfer fluid to an intravascular heat exchange catheter.

BACKGROUND

Under ordinary circumstances, thermoregulatory mechanisms exist in the healthy human body to maintain the body at a constant temperature of about 37° C. (98.6° F.), a condition sometimes referred to as normothermia. To maintain normothermia, the thermoregulatory mechanisms act so that heat lost to the environment is replaced by the same amount of heat generated by metabolic activity in the body.

For various reasons, however, a person may accidentally develop a body temperature that is above or below normal, conditions known as hyperthermia or hypothermia respectively. These conditions have generally been regarded as harmful and patients suffering from either condition have been treated to return them to normothermia by various mechanisms, including application of warming or cooling blankets, administration of hot or cold liquids by mouth, hot or cold liquids infused into the bloodstream, immersion of the patient in hot or cold baths, and directly heating or cooling blood during cardiopulmonary bypass.

Besides treating undesirable hypothermia to reverse the condition and restore normothermia, medical science recognizes that it is sometimes valuable to intentionally induce and maintain regional or whole body hypothermia for therapeutic reasons. The term "whole body hypothermia" refers to the condition where the whole body temperature, usually measured as the core body temperature, is below normothermia. "Regional hypothermia" refers to the condition where target tissue of one region of the body such as the brain or the heart is maintained at a temperature below normothermia. During regional hypothermia, the core body temperature may be normothermic, or may be slightly hypothermic but is generally warmer than the target tissue.

It may be desirable, for example, to induce whole body or regional hypothermia for the purpose of treating, or minimizing the adverse effects of, certain neurological diseases or disorders such as head trauma, spinal trauma and hemorrhagic or ischemic stroke. Additionally, it is sometimes desirable to induce whole body or regional hypothermia for the purpose of facilitating or minimizing adverse effects of certain surgical or interventional procedures such as open heart surgery, aneurysm repair surgeries, endovascular aneurysm repair procedures, spinal surgeries, or other surgeries where blood flow to the brain, spinal cord or vital organs may be interrupted or compromised. Neural tissue such as the brain or spinal cord, is particularly subject to damage by blood deprivation for any reason including ischemic or hemorrhagic stroke, cardiac arrest, intracerebral or intracranial hemorrhage, and head trauma In each of these instances, damage to brain tissue may occur because of brain ischemia, increased intracranial pressure, edema or other processes, often resulting in a loss of cerebral function and permanent neurological deficits. Hypothermia has also been found to be advantageous to protect cardiac muscle tissue during or after ischemia, for example during heart surgery or during or after a myocardial infarct.

Traditional methods inducing and/or maintaining hypothermia include application of surface cooling such as an ice bath or cooling blankets, infusing cold liquid into the vascular system of a patient, or controlling the temperature of a patient's blood during cardiopulmonary bypass. While each of these may be useful in certain settings, they each have significant disadvantages. For example, inducing hypothermia by placing a patient into a cold bath lacks precise control over a patient's core temperature and thus may result in harmful overshoot, which may be difficult if not impossible to reverse with any degree of control. It generally cannot be used in conjunction with surgery because sterility and access to the patient's body may make its use impractical or impossible. Cooling blankets are often too slow to cool the patient, or simply unable to overcome the body's natural ability to generate heat, particularly if the patient is shivering or experiencing vasoconstriction. Even if the patient is anesthetized, or has otherwise had his thermoregulatory responses impaired or eliminated, cooling by means of cooling blankets is still often too slow and inefficient to be useful. Control over the patient's temperature is generally poor, which is particularly dangerous if the patient's own thermoregulatory controls are eliminated or impaired.

Infusion of cold or hot fluid into a patient's bloodstream has also been used to affect the temperature of a patent. However, this procedure is severely limited because of the hazards of fluid loading. Particularly where hypothermia is to be maintained for a long period of time, continuous infusion of sufficient cold liquid to counter the heat generated by ordinary bodily activity creates an unacceptable amount of fluid introduced into the body. In addition, as with the methods described above, control over the patient temperature is limited.

Another method sometimes employed, especially during heart surgery, is cardiopulmonary bypass, where blood is removed from the body, oxygenated and returned to the circulatory system by means of a mechanical pump. While being circulated outside the body, the temperature of the blood may be controlled by directly heating or cooling it and then pumping it back into the body, and in this way the temperature of the entire body of the patient may be controlled. Because of the large volume of blood removed, treated, and pumped back into the body, heating or cooling the body by means of cardiopulmonary bypass is very rapid and may be precisely controlled. However, the use of an external mechanical pump to circulate blood tends to be very destructive of the blood and thus physicians try to minimize the time on which the blood is being subjected to this treatment, preferably to four hours or less. Furthermore, the situations in which the use of this method for temperature control is very limited because of the extremely invasive nature of cardiopulmonary bypass. The patient must be anesthetized, highly trained personnel are required, and the procedure is only available in an operating room or similarly equipped facility.

Intravascular heat exchangers have been developed to control patient temperature for either treating hypothermia or hyperthermia or inducing and maintaining hypothermia. The intravascular heat exchanger overcomes many of the shortcomings of the above mentioned methods while permitting the advantageous aspects of controlling patient temperature. The intravascular heat exchanger comprises a catheter in which heat transfer fluid is circulated between an external heat exchanger, such as a solid state thermoelectric plate of one or more Peltier cooling units and a heat transfer region such as a balloon region on the end of the catheter. The heat exchange region is inserted into the vasculature of a patient. The heat transfer fluid exchanges heat with the blood at the heat transfer region to change the temperature of the blood and thus of the patient. The heat transfer fluid is then circulated out of the body and exchanges heat with the external heat exchanger outside the body to add or remove the heat lost or gained from the blood. In this manner the temperature of the blood and ultimately of the patient may be controlled by controlling the temperature of the external heat exchanger.

Some intravascular heat exchange catheters may be designed to affect a small amount of tissue, for example a small bolus of blood in thermodilution catheters (see e.g. Williams, U.S. Pat. No. 4,941,475) or catheters designed to protect or affect the tissue in contact with the catheter (see e.g. Neilson, et al., U.S. Pat. No. 5,733,319). However, intravascular heat exchangers designed to affect whole or regional body temperature may be expected to exchange a significant amount of energy, for example more than 100 watts. This is achieved by maintaining a maximum difference in temperature between the blood and the heat transfer region ($\Delta T$), and flowing a maximum amount of heat exchange fluid through the circuit. A heat exchange fluid that can be maintained between 0° C. and 45° C. is generally preferable, along with a fluid supply system that can supply adequate flow of heat transfer fluid and temperature control of that fluid. Such systems ideally will also have one of more of the following properties: maximum external heat exchange ability, closed circuit for sterility, small volume for precise and rapid control of temperature, a system for pressure regulation to precisely control flow rate, optimal flow rate, disposable features, ease of handling, and reliability.

SUMMARY OF THE INVENTION

One aspect of the invention is a heat exchange fluid supply system for supplying a heat exchange fluid to an intravascular heat exchange catheter, which includes a disposable cassette having a pump head and an external heat exchanger. The configuration of the external heat exchanger is not intended to be structurally limited and may include a sack-like configuration, a relatively flat configuration with multiple paths therein, with a long serpentine path therein, or any other suitable configuration capable of mating with a heat generating or removing unit. The system may be configured to operate in combination with a reusable master control unit and an external fluid source.

Another aspect of the invention is a disposable cassette for supplying a heat exchange fluid to a heat exchange catheter, the cassette comprising: an external heat exchanger comprising a flow channel having an inlet and an outlet; a first fluid supply line, the first fluid supply line being in fluid communication with the flow channel inlet; a pump head contained in the disposable fluid supply cassette, and having a pump inlet and a pump outlet, where the pump inlet is in fluid communication with the external heat exchanger flow channel outlet for pumping fluid from the external heat exchanger flow channel outlet; a second fluid supply line, the second fluid supply line being in fluid communication with the pump outlet for receiving fluid pumped out of the pump outlet; and a pressure regulator, the pressure regulator being in fluid communication with the pump outlet for regulating the pressure of fluid pumped from the pump head.

Yet another aspect of the invention is a heat exchange fluid supply system for a heat exchange catheter, the system comprising: an external heat exchanger comprising a structural member and a compliant member, where the compliant member is sealed to the structural member in a pattern, the pattern forming a flow channel between the compliant member and the structural member, and the flow channel having an inlet and an outlet; a first fluid supply line, the first fluid supply line being in fluid communication with the flow channel inlet; a bulkhead, the bulkhead comprising a pump head and a reservoir, the reservoir having a reservoir inlet and a reservoir outlet, the reservoir inlet being in fluid communication with the external heat exchanger flow channel outlet, the pump head having a pump inlet and a pump outlet, the pump inlet being in fluid communication with the reservoir outlet for pumping fluid from the reservoir outlet; a second fluid supply line, the second fluid supply line being in fluid communication with the pump outlet for receiving fluid pumped out of the pump outlet; and an external fluid source, the external fluid source being in fluid communication with the bulkhead.

Still another aspect of the invention is a disposable cassette for supplying heat exchange fluid to a heat exchange catheter, the cassette comprising: an external heat exchanger having an inlet and an outlet; a first fluid supply line, the first fluid supply line in fluid communication with the heat exchanger inlet; a disposable pump head contained in the cassette, the pump head actuated by an electric motor, the pump head having an inlet and an outlet, and the pump inlet being in fluid communication with the heat exchanger outlet; a second fluid supply line, the second fluid supply line being in fluid communication with the pump outlet for receiving fluid pumped out of the pump outlet; and an optional pressure regulator, the pressure regulator being in fluid communication with the pump outlet for regulating the pressure of fluid pumped from said pump head.

Another aspect of the invention is a disposable cassette for supplying a heat exchange fluid to an intravascular heat exchange catheter, the cassette having a bulkhead and an external heat exchanger. The external heat exchanger has a thin heat exchanger layer and a back plate fused together to form a serpentine flow channel or a plurality of flow channels, and has an inlet orifice and an outlet orifice that allow fluid to circulate through the external heat exchanger and which communicate with the bulkhead. In one embodiment, the bulkhead has three components which can be independent sections coupled together or where at least two of the sections are housed together: a reservoir section, a feedblock section and a pump section. The reservoir section has an inlet hole leading from the external heat exchanger and an outlet leading to the feedblock section, a fluid reservoir for storage of heat exchange fluid, a fluid level detector for monitoring the level of heat exchange fluid within the fluid reservoir, a cover plate that functions to retain fluid within the reservoir and which is fitted with at least one vent hole into which is positioned a hydrophobic vent for releasing air contained within the fluid reservoir. The feedblock section has a central chamber which houses a priming valve that directs fluid flow, an inlet and corresponding inlet channel from the reservoir and an inlet and corresponding inlet channel from an external fluid source which both lead into the central chamber, an outflow channel leading from the central chamber to an outlet which is directed to the pump head, a flexible membrane covering the central chamber, a flow-through channel having an inlet which leads from the pump head and a fluid coupling outlet means for fluidly connecting the catheter to the bulkhead, and a flow-through channel having a fluid coupling inlet means for fluidly connecting the catheter to the bulkhead and an outlet which leads to the pump section and then to the external heat exchanger. The pump section has a quasi-cardioid shaped cavity, into which is positioned a rotor is fitted with a vane for moving fluid from an inlet and inlet channel to an outlet channel and outlet a wheel assembly to facilitate movement of the rotor and a flow-through channel having an inlet that leads from the feedblock section and an outlet which leads to the external heat exchanger.

In yet another aspect of the invention, the bulkhead has two components: a reservoir section and a pump section, where the pump and reservoir sections are configured similar to that described above, except that the outlet of the reservoir section leads to the pump section and the reservoir further comprises a pressure damper and an inlet in fluid communication with an external fluid source.

Still another aspect of the invention relates to a cassette for supplying heat exchange fluid to a heat exchange catheter, where the cassette comprises: (a) an external heat exchanger comprising a structural member and a compliant member, where the compliant member is sealed to the structural member in a pattern that forms a flow channel between the compliant member and the structural member, and where the flow channel has an inlet and an outlet; (b) a first fluid supply line in fluid communication with the flow channel inlet; (c) a bulkhead comprising a reservoir and a disposable pump head, where the reservoir contains an inlet in fluid communication with the flow channel outlet, and further has a fluid level detector for detecting the level of fluid within the reservoir, wherein the pump head is a cardioid vane pump head having an inlet and an outlet, and the pump head is actuated by an electric motor, where the pump inlet is in fluid communication with the reservoir outlet and the electric motor is controlled by an amplifier controller, where the amplifier controller supplies a constant current to the pump head thereby causing the pump head to supply a relatively constant pressure to the fluid in the second fluid supply line; (d) a second fluid supply line in fluid communication with the pump outlet for receiving fluid pumped out of the pump outlet; (e) an external fluid source in fluid communication with the reservoir; and (f) a pressure damper in fluid communication with the pump outlet.

Another aspect of the invention pertains to a method for providing a temperature regulated source of heat exchange fluid for heat exchange catheters, comprising the steps of: providing a circuit comprising an external heat exchanger, a pump, a heat exchange catheter, and air vents, where the external heat exchanger, pump and heat exchange catheter are in fluid communication such that fluid pumped by the pump is circulated through the heat exchange catheter and the external heat exchanger, and the air vents allow passage of gas in and out of the circuit through the vents but do not allow passage of liquid in and out of the circuit though the vents; providing a heat generating or removing unit in heat exchange relationship with the external heat exchanger; providing an external fluid source in fluid communication with the circuit; circulating heat exchange fluid from the external source through the circuit by means of pumping with the pump while simultaneously venting any gas contained in the circuit out through the air vents; and controlling the temperature of the heat exchanger fluid in the circuit by controlling the temperature of the heat generating or removing unit.

BRIEF DESCRIPTION OF THE DRAWING

FIG. 1 is an illustration of the disposable fluid supply cassette of the invention attached to a heat exchange catheter, external fluid source and positioned for insertion into a suitable reusable master control unit.

FIG. 2 is an illustration of the disposable fluid supply cassette and a reusable master control unit.

FIGS. 3 and 4 are exploded views of different embodiments of the disposable fluid supply cassette of the invention.

FIG. 4A is a perspective bottom view of a fitment of the invention.

FIG. 4B is a perspective top view of a fitment of the invention.

FIG. 4C is a cross-section of the external heat exchanger taken along line 4C-4C of FIG. 4 with no pressurized fluid therein.

FIG. 4D is a cross-section of the external heat exchanger taken along line 4C-4C of FIG. 4 with pressurized fluid therein.

FIG. 5 is a top plan view of the bulkhead of the disposable fluid supply cassette of FIG. 3.

FIG. 5A illustrates the fluid flow pathway.

FIG. 5B is a cross-sectional view of the reservoir section taken along line 5B-5B of FIG. 5.

FIG. 6 is a top plan view of the bulkhead of the disposable fluid supply cassette of FIG. 4.

FIG. 6A illustrates the fluid flow pathway.

FIG. 7 is an exploded view of the reservoir section of the bulkhead of FIG. 3.

FIG. 8 is an exploded view of the feedblock section of the bulkhead of FIG. 3.

FIG. 9 is an exploded view of the pump section of the bulkhead of FIG. 3.

FIG. 10 is an exploded view of the reservoir section of the bulkhead of FIG. 4.

FIG. 11A is a cross-sectional view of a printing valve of the shown invention shown with the valve stem relaxed and the valve in the normal operating position.

FIG. 11B is a cross-sectional view of a priming valve of the invention shown with the valve stem depressed and the valve in the auto-prep position.

FIG. 12A is a top plan view of the pump section of the invention.

FIG. 12B illustrates the geometry of the pump section.

FIG. 13 is a side cutaway view of the pump head of the invention taken along line 13-13 of FIG. 12A.

FIG. 14 is a top cut-away view of the pump wheels in place within the reusable master control unit.

FIG. 15 is a side view of the pump wheels in place within the reusable master control unit.

FIG. 16 is a top view of a pressure regulator valve of the invention.

FIG. 17 is a cross-sectional view of the throttle chamber taken along line 17-17 of FIG. 16.

FIG. 18 is a cross-sectional view of a pressure damper.

FIGS. 19A, 19B and 19C are schematic illustrations of the fluid flow using different embodiments of the disposable fluid supply cassette of the invention.

FIGS. 20A, 20B and 20C are side views of various embodiments of the pump vane.

DETAILED DESCRIPTION OF THE INVENTION

The invention relates to a heat exchange fluid supply system for supplying a heat exchange fluid to an intravascular heat exchange catheter, which includes a disposable cassette having a pump head and an external heat exchanger. The system is configured to operate in combination with a reusable master control unit and an external fluid source. The heat exchange fluid supply system of the invention is designed to provide an adequate supply of heat exchange fluid to the catheter at sufficient flow rate and to provide a convenient and efficient heat exchange means to adjust the temperature of the heat exchange fluid. This system is easy to handle, inexpensive and disposable, thus eliminating the need for extensive and time consuming sterilization between treatment of different patients. An additional feature of the cassette is that, due to its closed loop fluid path, sterility is maintained for the duration of operation of the catheter.

FIG. 1 illustrates the heat exchange fluid supply system of the invention which includes disposable components including a heat exchange catheter 160; a disposable heat exchange fluid supply cassette 5, which includes a pump head 139 and fluid housing 19; sensors 77, 78; and a dual channel flow line 169; as well as reusable components including a heat generating or removing unit 11, a pump drive mechanism 12 and various controls for the unit.

The heat exchange catheter 160 is formed with a catheter flow line 162 and a heat exchanger 163 which may be for example a heat exchange balloon operated using closed-loop flow of heat exchange medium. The catheter shaft may be formed with a working lumen 156 for injection of drugs, fluoroscopic dye, or the like, and for receipt of a guide wire 157 for use in placing the heat transfer catheter at an appropriate location in the patient's body. The proximal end of the shaft may be connected to a multi-arm adapter 151 for providing separate access to various channels in the catheter shaft. For example, one arm 152 may provide access to the working lumen 156 of the catheter shaft for insertion of a guide wire 157 to steer the heat transfer catheter to the desired location. Where the internal heat exchanger 163 is a heat exchange balloon for closed-loop flow of a biocompatible fluid that serves as the heat exchange medium 35, the adapter 151 may contain an arm 153 to connect an inlet flow line 150 to an inlet flow channel (not shown) within the catheter shaft, a separate arm 154 to connect an outlet fluid line 158 to an outlet flow channel (also not shown). The dual channel flow line 169 may contain both the inlet and outlet flow lines 150, 158 to connect the catheter flow line 162 to the disposable heat exchange fluid supply cassette 5. Additionally, one of the flow lines, for example the inlet flow line 150 may be connected to an external fluid source 15 of heat exchange medium 35 to prime the closed-loop heat exchange balloon catheter system as necessary. The external fluid source 15 may also be directly connected to the cassette 5, as is shown in other embodiments of the invention.

The heat exchange cassette 5 may include fluid housing 19 configured in a serpentine pathway for the heat exchange fluid to be pumped through the cassette by means of a disposable pump head 139. The heat exchange cassette, including the serpentine pathway and the pump head 139 is configured to install into a reusable master control unit 185. The master control unit may include a heat generating or removing unit 11 such as a solid state thermoelectric heater/cooler (TE cooler). A TE cooler is particularly advantageous because the same unit is capable of either generating heat or removing heat by changing the polarity of current activating the unit. Therefore it may be conveniently controlled to supply or remove heat from the system without the need of two separate units.

The master control unit includes a pump drive mechanism 12 that activates the pump head 139 to pump the heat exchange fluid 35 and cause it to circulate through the catheter's heat exchanger 163 and the serpentine path of the fluid housing 19 in the heat exchange cassette. When installed, the fluid housing 19 is in thermal communication with the TE cooler, and thus the TE cooler may act to heat or cool the heat exchange fluid as that fluid is circulated through the serpentine pathway. When the heat exchange fluid is circulated through the internal heat exchanger 163 located in a patient's body, it may act to add or remove heat from the body. In this way the TE cooler may act to affect the blood temperature of a patient as desired.

The TE cooler and the pump head are responsive to a control unit 13. The control unit receives data input through electrical connections 63, 64, 65 to numerous sensors, for example body temperature sensors 77, 78 that may sense temperatures from a patient's ear, brain region, bladder, rectum, esophagus or other appropriate location as desired by the operator who places the sensors. Likewise, a sensor 82 may monitor the temperature of the heat exchange balloon, and other sensors (not shown) may be provided as desired to monitor the blood temperature at the distal tip of the catheter, at the proximal tip of the balloon, or other desired location.

An operator by means of the manual input unit 14 may provide the operating parameters of the control system, for example a pre-selected temperature for the brain. These parameters are communicated to the control unit 13 by means of a connection between the manual input unit and the control unit. In practice, the operator using the manual input unit supplies a set of parameters to the control unit. For example, a desired temperature for the brain region and/or the whole body of the patient may be specified as the preselected temperature. Data is received from the sensors 77, 78 indicating for example, a sensed temperature of the patient at the location of the sensors, e.g. the actual core body temperature of the patient or the actual temperature of the brain region. Other data input may include the actual temperature of the heat exchanger, the temperature of blood at the distal end of the catheter body, or the like.

The control unit 13 coordinates the data and selectively actuates the various units of the system to achieve and maintain parameters. For example, it may actuate the TE cooler 11 to increase the amount of heat it is removing if the actual temperature is above the specified temperature, or decreasing the amount of heat being removed if the temperature is below the specified temperature. It may stop the pumping of the heat exchange fluid when the body or regional temperature sensed is the desired temperature, or it may stop pumping in response to other pre-determined criteria.

The control unit 13 may have a buffer range for operation wherein a target temperature is established, and an upper variance set point temperature and lower variance set point temperature are also set. In this way, the control unit may cause the heat exchanger to operate until the target temperature is reached. At that temperature, the control unit may suspend the operation of the heat exchanger until either the upper variance set point temperature is sensed or the lower variance set point temperature is reached. When the upper variance set point temperature is sensed, the control unit would then activate the heat exchanger to remove heat from the blood stream. On the other hand, if the lower variance set point temperature is sensed, then the control unit would activate the heat exchanger to add heat to the blood stream. Such a control scheme as applied to this system has the advantage of allowing the operator to essentially dial in a desired temperature and the system will act to reach that target temperature and maintain the patient at that target temperature. At the same time, a buffer range is established so that when the target temperature is reached, the control unit 13 will generally not turn the TE cooler 11 on and off or activate and deactivate the pump drive mechanism 12 in rapid succession, actions that would be potentially damaging to the electric units in question.

It may also be perceived, in keeping with the present invention, that the control unit 13 may be configured to simultaneously respond to several sensors, or to activate or deactivate various components such as several heat exchangers. In this way, for example, a control unit might heat blood that is subsequently circulated to the core body in response to a sensed core body temperature that is below the target temperature, and simultaneously activate a second heat exchanger to cool blood that is directed to the brain region in response to a sensed brain temperature that is above the target temperature. It may be that the sensed body temperature is at the target temperature and thus the heat exchanger that is in contact with blood circulating to the core body may be turned off by the control unit, while at the same time the control unit continues to activate the heat exchanger to cool blood that is directed to the brain region. Any of the many control schemes that may be anticipated by an operator and programmed into the control unit are contemplated by this invention.

An advantage of the system as illustrated is that all the portions of the system that are in contact with the patient are disposable, but substantial and relatively expensive portions of the system are reusable. Thus the catheter, the flow path for sterile heat exchange fluid, the sterile heat exchange fluid itself, and the pump head are all disposable. Even if a rupture in the heat exchange balloon permits the heat exchange fluid channels and thus the pump head to come in contact with a patient's blood, no cross-contamination will occur between patients because all those elements are disposable. The pump drive mechanism, the electronic control mechanisms, the TE cooler, and the manual input unit, however, are all reusable for economy and convenience. Likewise, the sensors may be disposable, but the control unit to which they attach is reusable.

The system of FIG. 1 can also be readily modified within the scope of the instant invention. For example, but not by way of limitation, the serpentine pathway may be a coil or other suitable configuration, the sensors may sense a wide variety of body locations and other parameters may be provided to the control unit, such as temperature or pressure, the heat exchanger may be any appropriate type, such as a thermal electric heating unit which would not require the circulation of heat exchange fluid. If a heat exchange balloon is provided, a pump head might be provided that is a screw pump, a gear pump, diaphragm pump, a peristaltic roller pump, or any other suitable means for pumping the heat exchange fluid. All of these and other substitutions obvious to those of skill in the art are contemplated by this invention.

In one embodiment of the invention, a disposable cassette for supplying a heat exchange fluid to a heat exchange catheter, comprises: an external heat exchanger comprising a structural member and a compliant member, where the compliant member is sealed to the structural member in a pattern, and the pattern forms one or more flow channels between the compliant member and the structural member, the flow channel having an inlet and an outlet; a first fluid supply line, the first fluid supply line being in fluid communication with the flow channel inlet; a pump head contained in the disposable fluid supply cassette, and having a pump inlet and a pump outlet, where the pump inlet is in fluid communication with the external heat exchanger flow channel outlet for pumping fluid from the flow channel outlet; a second fluid supply line, the second fluid supply line being in fluid communication with the pump outlet for receiving fluid pumped out of the pump outlet; and a pressure regulator, the pressure regulator being in fluid communication with the pump outlet for regulating the pressure of fluid pumped from the pump head.

Referring to FIGS. 1-4, an exemplary disposable cassette 5 for supplying a heat exchange fluid 35 to a heat exchange catheter 160 is shown. The cassette 5 comprises an external heat exchanger 20. The external heat exchanger can any be a combination of one or more structural and compliant members such that the overall configuration of the external heat exchanger is adapted to mate with the heat generating or removing unit. In a preferred embodiment, the structural member is a back plate 26 and the compliant member is heat exchange layer 28. The heat exchange layer is sealed to the back plate in a pattern which forms a flow channel 34 between the back plate and the heat exchange layer, and the flow channel has an inlet 36 and an outlet 38.

The cassette 5 also includes a first fluid supply line that is in fluid communication with the flow channel inlet 36. The pump head 139 has a pump inlet 113 and a pump outlet 115, where the inlet in fluid communication with the external heat exchanger flow channel outlet 38 and serves to pump fluid from the flow channel outlet. A second fluid supply line is in fluid communication with the pump outlet 115 and receives fluid that is pumped out of the outlet. The cassette 5 also includes a pressure regulator that is in fluid communication with the pump outlet. The disposable cassette is configured such that when the first and second fluid supply lines are connected to a heat exchange catheter, a fluid circuit is created and includes the external heat exchanger, pump head, the fluid lines and the catheter.

In another embodiment of the invention, a heat exchange fluid supply system for a heat exchange catheter comprises: an external heat exchanger comprising a structural member and a compliant member, where the compliant member is sealed to the structural member in a pattern, the pattern forming a flow channel between the compliant member and the structural member, and the flow channel having an inlet and an outlet; a first fluid supply line, the first fluid supply line being in fluid communication with the flow channel inlet; a bulkhead, the bulkhead comprising a pump head and a reservoir, the reservoir having a reservoir inlet and a reservoir outlet, the reservoir inlet being in fluid communication with the external heat exchanger flow channel outlet, the pump head having a pump inlet and a pump outlet, the pump inlet being in fluid communication with the reservoir outlet for pumping fluid from the reservoir outlet; a second fluid supply line, the second fluid supply line being in fluid communication with the pump outlet for receiving fluid pumped out of the pump outlet; and an external fluid source, the external fluid source being in fluid communication with the bulkhead. Referring more particularly to the cassette shown in FIGS. 3 and 4, and the overall system of FIG. 2, this system comprises the external heat exchanger 20 and fluid supply lines as described above. In addition, the cassette comprises a bulkhead (30, 330) that comprises a pump head 140 and a reservoir (58, 358). The reservoir has a reservoir inlet that is in fluid communication with the external heat exchanger flow channel outlet 38 and a reservoir outlet (62, 362). The pump head has a pump inlet 113 and a pump outlet 115, and the pump inlet is in fluid communication with the reservoir outlet (62, 362) for pumping fluid from the reservoir outlet. The heat exchange fluid supply system also can include an external fluid source 15 that is in fluid communication with the bulkhead.

One embodiment of the invention is a heat exchange fluid supply system for supplying a heat exchange fluid to an intravascular heat exchange catheter, which includes a disposable cassette having a bulkhead and an external heat exchanger. The bulkhead includes a reservoir section and a pump section which are in fluid communication with each other. The reservoir section is provided with a means to monitor the amount of heat exchange fluid that is in the system. The system may optionally comprise a mechanism for priming the system with heat exchange fluid from an external source and for circulating fluid to the catheter in a closed circuit, which is preferably a valve having a first position whereby the system is primed with heat exchange fluid from an external source and a second position where the fluid is circulated to the catheter in a closed circuit. In the absence of this valved-priming system, the system is passively primed. The pump section is configured to allow for pumping of heat exchange fluid at a constant pressure. This aspect of the invention is illustrates in FIG. 2, which shows one embodiment of the disposable heat exchange fluid supply cassette 10 having a bulkhead 30 and an external heat exchanger having an inlet and an outlet, depicted in FIG. 2 as external heat exchanger 20. The cassette is configured to operate in combination with a reusable master control unit 186, which will typically be provided with a power supply and a heat generating or removing unit, and other parts that cooperate with the cassette 10, the details of which will be described in detail below.

One embodiment of the cassette of the invention is shown in FIG. 3 and includes a disposable fluid supply cassette 10 has an external heat exchanger 20 coupled to a bulkhead 30 by means of a cover plate 168. The bulkhead includes a reservoir section 40, an optional feedblock section 80 and a pump section 100, the details of which are described below. The sections can be independent and discrete units that are coupled together, as shown in FIG. 2. The invention also contemplates housing more than one section together in a single unit This may be desired for ease in manufacturing and assembly. The sections can be machined, molded or cast and are typically of a durable material such as plastic or Plexiglas.

The feedblock is configured to communicate with an external fluid source 15, which can be any suitable source of biocompatible fluid, by means of an external fluid providing line 16.

The fluid line 16 may be provided with a pinch clamp 21. The source of biocompatible fluid can be for example, an IV bag of saline. Bag size is not critical but has a typical capacity of about 250 ml. In addition, the feedblock communicates with an intravascular heat exchange catheter 160, by means of fluid supply line 150 and fluid return line 158. The external fluid providing, fluid supply and fluid return lines are typically of a flexible compressible material such as polyvinylchloride or other suitable flexible compressible tubing material. The disposable fluid supply cassette 10 can be packaged with or separately from the heat exchange catheter 160.

Another embodiment of the disposable heat exchange fluid supply cassette of the invention is shown in FIG. 4. The disposable fluid supply cassette 310 has an external heat exchanger 20 coupled to a bulkhead 330 by means of a cover plate 368. The bulkhead includes a reservoir section 340 and a pump section 300. The reservoir section 340 is configured to communicate with the external fluid source by means of an external fluid providing line. In addition, the pump section 300 communicates with the intravascular heat exchange catheter by means of a fluid supply line and a fluid return line.

The cassette of the invention is initially primed, that is, filled with heat exchange fluid from an external source and excess air removed. This priming of the system of the invention can be accomplished in numerous ways. One embodiment of the invention utilizes a "valved-priming" mechanism, and is illustrated by the embodiment of FIG. 3. This valved-priming mechanism involves a priming sequence having a valve or the like controlling temporary fluid input from an external fluid source, and once the system is primed, the valve prevents further fluid input from the external source and the fluid flow becomes a closed circuit within the cassette 10 and the catheter 160. In the embodiment of FIG. 3, the valved-priming mechanism is contained within a discrete unit referred to as the feedblock section. It is understood however, that the valved-priming mechanism can be located in another portion of the bulkhead, for example as part of the pump or reservoir section, and still serve the same function. During priming, heat exchange fluid from external fluid source 15 flows through the external fluid providing line 16 and enters the feedblock section 80, and then flows into the pump section 100. From the pump section, the fluid is pumped out through fluid supply line 150, which is coupled to the catheter inlet of the heat exchange catheter 160. It is thereafter circulated through the catheter, back through the fluid return line 158 to the external heat exchanger 20, through the external heat exchanger and into the reservoir. As the fluid is pumped into the reservoir, air displaced by the fluid escapes through the hydrophobic vents 54. This generally continues until the system is full of heat exchange fluid and excess air has been vented out of the system. At this point in the process, the valve is closed from the external fluid source and the fluid supply circuit between the catheter and the cassette is a closed circuit. This priming occurs prior to the insertion of the heat exchange catheter into the patient, with the heat exchange balloon outside the body. The valved-priming is described in greater detail below in connection with FIGS. 5, 8, 11A and 11B.

Another embodiment of the invention utilizes a "passive-priming" mechanism and is illustrated by the embodiment of FIG. 1 and FIG. 4. This passive-priming mechanism involves fluid input from the external fluid source 15, which serves to fill the system. The external fluid source 15 is generally hung or placed at a location above the reservoir, and is connected by means of an external fluid providing line 16 directly or indirectly to the reservoir in the cassette 310. Fluid moves into the reservoir, the pump is activated, and as described above in conjunction with the valved-priming, the fluid is pumped through the system and excess air is expelled out through the hydrophobic vents 54. Once the system is primed, the amount of fluid needed to maintain the system in a full condition may change slightly due primarily to changes in the compliance of the system at different temperatures. To accommodate this, additional fluid may enter the system from the external fluid source to maintain the filled condition, and similarly, excess fluid may leave the system and reenter the external fluid source. This has the advantage of maintaining a relatively uniform fluid level by automatic action. As with the valved-priming, this is generally done before the catheter is inserted, with the balloon outside the patient's vascular system.

As indicated above, the disposable cassette comprises an external heat exchanger, which is formed of a combination of one or more structural and compliant members. In a preferred embodiment, the structural member is a stiff back plate 26 and the compliant member is a flexible heat exchange layer 28, which are fused together to form a serpentine flow channel or a plurality of flow channels, and having an inlet orifice and an outlet orifice that communicate with the bulkhead. The external heat exchanger is positioned so as to be in a heat transfer relationship with a heat generating or removing unit provided in the reusable master control unit, as shown in FIGS. 1 and 2. There are numerous heat exchangers that can be used with the disposable cassette of the invention. Due to the configuration of the external heat exchanger, the heat generating or removing unit is preferably a flat thermally conducting plate which is heated or cooled to add or remove heat from the heat exchange fluid.

Turning to FIG. 4, the external heat exchanger 20 is shown as having two layers, a relatively stiff back plate 26 that functions as a structural member and a thinner heat exchange layer 28 that functions as the compliant member. The back plate 26 is typically made of a high density polyethylene and is generally about 0.030 inches (30 mils) thick. The thinner heat exchange layer is shown in this embodiment as being sealed in a serpentine pattern to the back plate by fusing such as by heat sealing or other suitable technique to permanently adhere the two layers together. The pattern of heat sealing creates a serpentine pathway composed of sealed portions 32 separating a serpentine flow channel 34 or a plurality of flow channels. The sealed portions 32 provide for the channels 34 to be continuous. The winding flow channels 34 form a pathway which causes the heat exchange fluid to flow back and forth adjacent to and in heat transfer relationship with the heat generating or removing unit, and ensures that the fluid circulates proximate to the heat generating or removing unit for a sufficient amount of time to allow for adequate heating or cooling of the fluid. The invention also encompasses utilizing sealed portions that are not continuous, as long as the sealed portions are configured so as to create channels that permit fluid flow through the external heat exchanger 20. In addition, the external heat exchanger can be configured to have a V-shaped leading edge 23 that acts as a guide to facilitate placement into the control unit 186.

The thinner heat exchange layer is generally about 4 to 8 mils, and is typically a low density polyethylene material, and is slightly elastomeric or compliant so that when pressurized heat exchange fluid 35 is placed into the legs of the channels, they bow out slightly as may be seen in FIGS. 4C (uninflated) and 4D (inflated). Since the back plate 26 and thinner heat exchange layer 28 are both polyethylene, they weld together effectively by means of heat welding. However, the bulkhead 330 is not the same material, and therefore the external heat exchanger is sealed to the bulkhead by other means, such as by a mechanical pressure seal.

The external heat exchanger 20 is provided with an extended attachment 48 whereby the external heat exchanger may be sealed to the bulkhead 330. The extended attachment 48 has three sections, a first flap section 142, a cutaway section 144 and a second flap section 146. One or more vent holes 52 are cut into the first flap section 142 to allow air to vent from the corresponding number of hydrophobic gas permeable vents 54 over a fluid reservoir, as will be described in greater detail below. While a plurality of vent holes 52 is shown in the embodiment of FIG. 4, any suitable shape or number of holes will suffice, for example a single vent hole is shown in the embodiment of FIG. 3.

The external heat exchanger 20 also has an inlet orifice 36 and an outlet orifice 38, which allows the heat exchange fluid to exit the bulkhead, circulate through the external heat exchanger (positioned in a heat transfer relationship with a heat generating or removing unit) and then enter the bulkhead after being heated or cooled. Each orifice is provided with a fitment that allows fluid to flow into the space between the thin heat exchange layer 28 and the back plate 26. When heat exchange fluid is pumped into the inlet orifice 36 through a first fitment 22, it winds its way along the serpentine path to outlet orifice 38 and then enters the bulkhead through a second fitment 24. The entire external heat exchanger is lain on a hot or cold plate of a heat generating or removing unit such as the heat exchange surface of a thermoelectric cooler, with the thinner heat exchange layer 28 positioned against the hot or cold plate. In this way, the temperature of heat exchange fluid may be controlled by controlling the temperature of the hot or cold plate and pumping fluid through the external heat exchanger.

Fitments 22, 24 are secured within the inlet and outlet orifices 36, 38. The fitments are constructed as illustrated in FIGS. 4A and 4B for fitment 24. Each fitment has a bored channel, a base plate 44, and a plurality of spacer protrusions 46 on the lower surface of the base plate. The embodiment of FIG. 4B illustrates four such protrusions but the invention contemplates having fewer or more than four protrusions. When the fitments are placed in the external heat exchanger, the channel exits the orifice, and the base plate is tightly positioned between the heat exchange layer 28 and the back plate 26. The spacer protrusions space the base plate away from the back plate of the external heat exchanger so that fluid contained within channels 34 passes between the protrusions, through fitment channel 37, and then into bulkhead 330. Similarly, fluid returning from the heat exchange catheter enters channels 34 through a bored channel in fitment 22, passes between the protrusions and flows into the channels. Two O-rings, such as flexible rubber washers, can be positioned around the periphery of the top section 148 of each fitment and are positioned between the heat exchange layer 28 and the bulkhead 30. The reservoir section has an inlet hole 56, while the pump section has an outlet hole 57. The fitment top section 148 of fitment 24 is sized to be inserted into inlet hole 56 and the corresponding top section of fitment 22 is sized to be inserted into outlet hole 57.

FIGS. 7, 8 and 9 are exploded views of the bulkhead 30 of the embodiment of FIG. 3 and its components, while FIGS. 5 and 5A illustrate the assembled bulkhead 30. Similarly, FIG. 10 is an exploded view of one of the reservoir section 340 component of the bulkhead 330 of the embodiment of FIG. 4, while FIGS. 6 and 6A illustrate the assembled bulkhead 330.

Referring to FIGS. 7, 5 and 5A, the reservoir section 40 has an inlet hole 56 leading from the external heat exchanger 20 and an outlet channel 62 leading to the feedblock section 80, a fluid reservoir 58 with an indented area 60 for storage of heat exchange fluid, a fluid level detector 69 for monitoring the level of heat exchange fluid within the fluid reservoir, an optional mounting block 75 for positioning of an optional pressure regulator valve useful for controlling the pressure for heat exchange fluid flow from the feedblock section to the catheter, a reservoir cover plate 53 that serves to retain fluid within the reservoir. The cover plate 53 seals the reservoir but is fitted with one or more vent holes 55 into which are positioned a corresponding number of hydrophobic gas permeable vents 54 for releasing air contained within the fluid reservoir. The reservoir section 40 of FIG. 5 also is shown with a mounting block 75 for the pressure regulator valve 76. The function of the pressure regulator will be described in greater detail below. The fluid reservoir 58 can also be configured so as to have an indented area 60 in the base, optionally covered with a partial lid 61. The lid 61 provides a fluid tight cover over the indented area except for a slit 59 which is open between the indented area 60 and the interior of the reservoir in an area near the prisms 69, 74. In this way the fluid opening leading to the reservoir outlet channel is located near the prisms and the prisms will most accurately reflect the fluid level available to the feedblock and thus the pump. This is seen in the embodiment of FIG. 5B. Heat exchange fluid enters the fluid reservoir 58 from the inlet hole 56, collects in the reservoir and then flows into the reservoir outlet channel 62. The reservoir outlet is at the base of the fluid reservoir 58 and is fluidly connected to an inlet 87 and inflow channel 86 of the feedblock section. This may be accomplished by the snug fitting of an outlet collar 66 at the outlet channel 62 from the reservoir over a cylindrical protrusion 68 of the feedblock section inlet.

Referring to FIGS. 8, 5 and 5A, the feedblock section 80 has a central chamber 90 which houses a priming valve 84 that directs fluid flow, an inlet 87 and corresponding inlet channel 86 from the reservoir and a fill port 18 and filling channel 88 from an external fluid source which both lead into the central chamber, an outflow channel leading 92 from the central chamber to an outlet 93 which is directed to the pump, a flexible membrane 96 covering the central chamber, an optional pressure regulator chamber 198 adjacent to an optional sensing chamber 224 (having a diaphragm 204 and push rod 210) which communicates with the pressure regulator valve when present, an optional pressure damper (not shown), an outlet channel 219 leading from the sensing chamber or damper to a fluid coupling outlet means 149 in the feedblock section for fluidly connecting the bulkhead to the catheter fluid supply line 150, an inlet 95 and channel 196 which connects the pump to the sensing chamber or damper, and a flow-through channel 221 having a fluid coupling inlet means 159 for fluidly connecting the catheter fluid return line 158 to the bulkhead and an outlet 97 which leads to the pump section and then to the external heat exchanger. The priming valve 84 can be any suitable mechanism and is illustrated in the embodiment of FIGS. 8, 5 and 5A as a spool valve.

Referring to FIGS. 10, 6 and 6A, the reservoir section 340 has an inlet hole 56 leading from the external heat exchanger 20 and an outlet channel 362 leading to the pump section 300, a fluid reservoir 358 for storage of heat exchange fluid, a fluid level detector 369 for monitoring the level of heat exchange fluid within the fluid reservoir, a reservoir cover plate 353 that serves to retain fluid within the reservoir. The cover plate 353 seals the reservoir but is fitted with a one or more vent holes 55 into which are positioned a corresponding number of hydrophobic gas permeable vents 354 for releasing air contained within the fluid reservoir. The reservoir section 340 also has a fill port 318 connected to an external fluid source, and a pressure damper, which comprises a pressure dampening chamber 230 filled with a compressible material 232. The reservoir section is fitted with a collar 371 that couples the dampening chamber to the pump section.

The pressure of fluid flowing from the bulkhead to the catheter through fluid supply line 150, can be controlled in numerous ways. In the embodiment of FIG. 3 the pressure is controlled by a pressure regulator valve. However, a pressure regulator valve and the chambers that operate with it are optional features and may be replaced by a constant current system and a pressure damper, which is illustrated in FIG. 18.

In the embodiment of the invention having a pressure regulator valve, the fluid supply system is configured to have a reservoir section, a feedblock section and a pump section, where the pressure regulator is contained within the feedblock section. It is understood however, that the pressure regulator can be located in another portion of the bulkhead, for example as part of the pump or reservoir section, and still serve the same function. The pressure regulator comprises the pressure regulator valve that controls the pressure of the fluid flow from the feedblock section to the catheter mounted in the reservoir section. The pressure regulator also comprises a pressure regulator chamber (having a counter spring and counter spring block) adjacent to a sensing chamber (having a diaphragm and push rod) which communicates with the pressure regulator valve. Both the pressure regulator chamber and the sensing chamber are housed in the feedblock section. The feedblock section also has an outlet channel leading from the sensing chamber to an outlet in the feedblock section which leads to the catheter and an inlet and inlet channel which connects the pump to the sensing chamber. One embodiment of the pressure regulator is shown in the embodiments of FIGS. 5 and 5A, where the reservoir section 40, feedblock section 80 and pump section 100 are shown as being coupled together, and the pressure regulator comprises the pressure regulator valve 76, a pressure regulator chamber 198 (with counter spring 222 and counter spring block 220) adjacent to a sensing chamber 224 (with a diaphragm 204 and push rod 210) which communicates with the pressure regulator valve. An outlet channel 219 on the feedblock section leads from the sensing chamber to a fluid coupling outlet means 149 in the feedblock section and serves to fluidly connect the bulkhead to catheter fluid supply line 150, while an inlet 95 and inlet channel 196 connects the pump to the sensing chamber.

The pump head can be any type such as is well known in the art, for example, a vane pump, a diaphragm pump, a peristaltic pump, an impeller pump, a gear pump and so forth. A preferred embodiment utilizes a cardioid vane pump, as shown in FIGS. 5 and 9. The pump section 100 has a quasi-cardioid shaped cavity 104, into which is positioned a pump head 140 that comprises a rotor 106, a vane 110 for moving fluid from an inlet 113 and inlet channel 112 to an outlet channel 114 and outlet 115, a wheel assembly for coupling to the motor and to facilitate movement of the pump head, for example a plurality of wheels 134, 136, and 138, and a flow-through channel 143 having an inlet 141 that leads from the feedblock section 80 and an outlet hole 57 which leads to the external heat exchanger 20. Referring to the embodiment shown in FIG. 6, the pump section 300 has the same shaped cavity 104 and pump head parts as described for the embodiment of FIG. 5. The vane 110 moves fluid from inlet 113 and inlet channel 112 to the pump outlet channel 314. The pump section 300 also has a flow-through channel 343 having a fluid coupling inlet means 159 that leads from the catheter and an outlet hole 57 which leads to the external heat exchanger 20. The pump outlet channel 314 is independently in fluid communication with a pressure dampening chamber 230. Outlet channel 314 is also configured with a fluid coupling outlet means 149 for fluidly connecting the bulkhead to the catheter. Fluid moving along this pathway encounters an opening 250 that exposes the fluid to the compressible material 232 within the dampening chamber. The pump is able to pump fluid through the system at pressure in excess of 35 psi. More critical to the invention, the pump is able to rapidly achieve and maintain a predetermined pressure, for example 40 psi.

In the embodiment of FIGS. 3 and 7-9, the reservoir section 40 is shown as being coupled to the feedblock section 80 which in turn is shown as being coupled to the pump section 100; however, at least two of these sections can be housed together in one unit. These sections can be readily coupled as follows. The reservoir section 40 has two collars: outlet collar 66 and pressure regulator collar 67. These fit tightly over two collars of slightly smaller size positioned on the feedblock section, the inlet collar 85 and sensing chamber collar 225. The feedblock section has three additional collars: outlet collar 81, inlet collar 83 and outlet collar 89, around which are positioned O-rings 228. Collar 81 fits snugly with inlet 141, collar 83 fits snugly with outlet 115 and collar 89 fits snugly with inlet 113. In the embodiment of FIGS. 4 and 10, the reservoir section 340 is readily coupled to the pump section 300 by means of a collar 371 on the reservoir section that fits into a matching sleeve on the pump section 300, and an outlet channel 362 that fits in the bottom of an L-shaped channel on the pump section. Any of the aforementioned sections in FIGS. 3 and 4 may further be secured with appropriate adhesive if desired.

The reservoir section can be provided with a means to monitor the amount of heat exchange fluid that is in the system, more specifically an optical means for detecting the level of fluid contained within the fluid reservoir. Since the heat exchange fluid is a biocompatible fluid and the volume of the external source is about 250 ml, it is not expected that fluid leakage into the patient will be problematic. However, the heat exchange fluid supply system of the invention is designed to detect the level of the fluid in the system so that a warning or other measure can be instituted if the system becomes unacceptably low.

Accordingly, in one aspect of the invention, the reservoir section is provided with a means to detect the fluid level in the reservoir and comprises at least one prism mounted within the reservoir section adjacent the inside of a relatively transparent window or wall portion in the reservoir, and at least one optical beam source and at least one optical beam sensor mounted on the reusable master control unit adjacent the outside of the window.

In one embodiment, the fluid level detector comprises a prism mounted in the reservoir, a light beam source and a light beam sensor. The prism has a diffraction surface and the light beam source directs a light beam against that surface. The prism is configured so that when the diffraction surface is in contact with air, the light beam is reflected to impinge on the light beam sensor and the sensor generates a signal. Likewise, when the diffraction surface is in contact with fluid, the light beam does not reflect to the sensor and the sensor does not generate a signal.

In operation, a light beam is directed through the reservoir section and against the prism at a particular point along its angled length. The sensor is located to detect the presence or absence of a reflected beam. As long as the fluid reservoir remains fill and the fluid level is at a pre-determined elevation above the point of impingement of the light beam, the diffraction surface of the prism at that point is in contact with the fluid. Therefore, the light beam directed at the prism travels through the prism and, upon reaching the diffraction surface, is reflected such that the sensor does not observe a reflected beam. If the fluid falls below the pre-determined elevation, the diffraction surface of the prism at the point where the beam impinges on it will no longer be in contact with the fluid and will be in contact with air instead. Air has a different index of refraction than the index of refraction of the fluid. Accordingly, upon reaching the diffraction surface, the reflected beam will no longer reflect out to the same point, and is reflected in such a manner that it impinges upon the sensor, which will then observe a reflected beam.

In a preferred embodiment, two prisms, each having a corresponding beam source and beam, are utilized. Each prism will have a corresponding beam source and sensor mounted on the reusable master control unit at a location adjacent to the prism. For example, FIG. 2 illustrates placement of an optical beam source 166 and optical beam sensor 167 for the first prism 72 in the bulkhead design of FIG. 3. An adjacent beam source and sensor would also be provided for the second prism 74, if present. For the bulkhead design of FIG. 4, the beam source(s) and sensor(s) would be position on the control unit 186 at a location underneath the fluid level detector 369. The second prism/source/sensor is redundant and functions to monitor the same fluid level as the first prism but operates as a safety mechanism in the even the first prism/source/sensor fails to function properly. Alternatively, one of the prisms may also have a "high level" sensing system that can be used to signal the control unit when the fluid in the reservoir reaches a certain high level. This is useful, for example, when the valved-priming system is used and detection of a high or full level is needed to determine when to activate the valve to stop the priming sequence.

Referring to FIG. 7, a relatively transparent bulkhead material or a relatively transparent window 70 configured in the bulkhead allows for optical observation of the fluid level in the fluid reservoir 58 through the end of the reservoir section 40. First and second prisms 72, 74 are mounted at the end of the fluid reservoir near the inlet hole 56. In the embodiment of FIG. 9, first and second prisms 372, 374 are mounted within the fluid reservoir near the pressure dampening chamber 230. These prisms have a diffraction surface and may be machined separated and then affixed within the reservoir section or they may be machined as part of the section, and are made of a material such as polycarbonate. Although only one prism is needed for the fluid level detection method to function, it may be desirable to include a second redundant prism as described above.

If desired, both high level and low level sensors can be employed on each prism. The sensors will generate a signal indicating that either there is or is not fluid at the level of the optical beam. If the optical beam source and sensor are positioned or the optical beam is directed near the top of the tank, the indication that the fluid has reached that level will trigger the appropriate response from the control system, for example to terminate a fill sequence. On the other hand, if the sensor is positioned or optical beam directed to sense the fluid level on the bottom of the tank, then the fluid level detector is configured to detect a low fluid level and can generates a signal representing such low level. The cassette can then be configured to respond to this signal indicative of a low level of fluid in the reservoir. For example, the pump head can be designed to be responsive to this signal such that the pump head stops pumping when a low fluid level is detected, so that air will not be pumped into the heat exchange catheter.

In a preferred embodiment of the invention, the reservoir section is provided with a means to detect when the fluid reservoir is too low. In operation, the optical beam source is turned on to produce an optical beam that is directed towards the bottom of the prism and is reflected back to the optical beam sensor. Typically, this source would begin operation after the reservoir had started to fill with fluid. Thus, fluid would be in the reservoir and so the sensor will not observe a reflected light beam. As long as this is the case, the pump will continue to operate, moving fluid through the cassette and catheter. However, if the fluid level drops below the level of the optical beam, the sensor then will observe a reflected light beam, which will trigger the pump to cease operation and the system to shut down.

In the embodiment of the invention that involves a valved-priming sequence, the optical beam source is turned on to produce an optical beam that is directed towards the top of the prism and is reflected back to the optical beam sensor. As long as the sensor observes a reflected light beam, the fill operation of the cassette continues to run. As the fluid level rises, at some point it reaches a level such that the optical beam is deflected and no longer reflects back to the sensor. When the sensor no longer observes a reflected light beam, the fill operation of the cassette ceases.

This is illustrated by referring to FIGS. 8, 11A and 11B, where the bulkhead is shown as further comprising a chamber 90 that houses a valve 84. The chamber has a first chamber inlet 18 that is in fluid communication with the external fluid source 15, a second chamber inlet 87 in fluid communication with the reservoir outlet 62, and a chamber outlet 93 in fluid communication with the pump inlet 113. The valve is designed to have a first position whereby the first chamber inlet is open, the second chamber inlet is closed and fluid flows from the external fluid source to the pump inlet. In the second position of the valve, the first chamber inlet is closed, the second chamber inlet is open and fluid flows from the reservoir outlet to the pump inlet. In this embodiment, the fluid level detector is configured to detect a low fluid level and a high fluid level, and the detector generates a first signal representing the low level and a second signal representing the high level. Initially, the valve is in its first position and is maintained in this first position in response to the first signal thereby allowing fluid to enter reservoir until it reaches a high level, at which point the detector generates a second signal, and the valve is actuated to its second position.

FIGS. 5 and 6 also provide another view of the three hydrophobic gas permeable vents 54 located in the top of the reservoir section 40 and 340, and positioned over the fluid reservoir 58 and 358. These vents serve to purge air from the fluid supply by allowing gas such as air to escape, but will not vent fluid. In this way, as the fluid reservoir fills up, the air in the reservoir can be vented to the atmosphere, while not permitting any heat exchange fluid to escape. In addition the pore size on the vents is small enough to prevent the entrance of any contaminants such as microbes, thus maintaining the sterility of the fluid that is being circulated through the catheter in the patient's body.

One embodiment of the invention pertains to a method for providing a temperature regulated source of heat exchange fluid for heat exchange catheters, comprising the steps of: providing a circuit comprising an external heat exchanger, a pump, a heat exchange catheter, and air vents, where the external heat exchanger, pump and heat exchange catheter are in fluid communication such that fluid pumped by the pump is circulated through the heat exchange catheter and the external heat exchanger, and the air vents allow passage of gas in and out of the circuit through the vents but do not allow passage of liquid in and out of the circuit though the air vents; providing a heat generating or removing unit in heat exchange relationship with the external heat exchanger; providing an external fluid source in fluid communication with the circuit; circulating heat exchange fluid from the external source through the circuit by means of pumping with the pump while simultaneously venting any gas contained in the circuit out through the air vents; and controlling the temperature of the heat exchanger fluid in the circuit by controlling the temperature of the heat generating or removing unit.

This method may also include the step of providing a valve between the external fluid source and the circuit, where the valve has an open position which permits the flow of heat exchange fluid from the external fluid source into the circuit and a closed position which prevents the flow of heat exchange fluid from the external fluid source to the circuit. The method may also include use of a level sensor within the circuit to sense when the fluid level in the circuit is full, and where the level sensor generates a signal in response to the full fluid level. In combination with the valve, this method contemplates initially maintaining the valve in its open position until the sensor senses that the fluid level in the circuit is at an adequately full level and operating the valve into the closed position in response to such signal.

The method of providing a temperature regulated source of heat exchange fluid can also include the step of controlling the pressure of the fluid as the fluid is circulated through the circuit. This pressure control can be a pressure regulator in fluid communication with the circuit, for example a pressure damping mechanism. This pressure control can also be achieved by using a pump that is operated by an electric motor and maintaining a predetermined current to the electric motor.

Referring to FIGS. 19A and 19B, one method of supplying heat exchange fluid to an intravascular heat exchange catheter is illustrated by fluid flow pathway, each pathway illustrating a different embodiment of the cassette of the invention. In both embodiments, fluid flows from the pump to the heat exchange catheter. The fluid returns from the catheter, passes through the external heat exchanger, and then enters a fluid reservoir. From the reservoir, the fluid moves to the pump, and the cycle repeats for the desired duration. An optional pressure regulator can be position in the fluid path moving from the pump to the catheter. Fluid is provided from an external fluid source, which in the embodiment of FIG. 19A enters the priming valve, and in the embodiment of FIG. 19B enters the pump head.

Examples of these methods and the respective fluid pathways are further understood by reference to FIGS. 5A and 6A. In general, this method comprises the steps of: (a) providing power to operate a pump head; (b) transferring fluid from an external fluid source to a chamber; (c) pumping fluid from the chamber into a pump cavity; (d) pumping fluid from the pump cavity to the catheter; (e) pumping fluid from the catheter to a external heat exchanger which is positioned in heat transfer relationship with a heat generating or removing unit; (f) pumping fluid from the external heat exchanger to a heat exchange fluid reservoir; (g) pumping fluid from the heat exchange fluid reservoir into the pump cavity; and (h) repeating steps (d) through (g) for the duration of operation of the catheter. Preferably a step for measuring the fluid level in the heat exchange fluid reservoir is included. Such step can be used to insure that the reservoir remains full. Such step can also comprise using an optical fluid level detector to determine the fluid level, where step (h) begins when the reservoir is filled to capacity and step (b) ceases when step (h) begins. The method for supplying heat exchange fluid to a catheter using the embodiment of FIG. 6A uses a passive-priming mechanism, while the embodiment of FIG. 5A uses a unique valved-priming mechanism, which is described in detail below. In the priming mechanism shown in FIG. 5A, the fluid level measuring step may also comprise using an optical fluid level detector to determine the fluid level, where step (g) begins when the reservoir is filled to capacity and step (b) ceases when step (g) begins.

Referring to the bulkhead embodiment of FIG. 6A and the flow diagram of FIG. 19A, a method for supplying heat exchange fluid to an intravascular heat exchange catheter comprises the steps of: (a) transferring fluid from an external fluid source 15 to a chamber, which is the heat exchange fluid reservoir 358; (b) providing power to operate a pump head 140 (c) venting air from the heat exchange fluid reservoir as the air is displaced by the fluid from the external fluid source; (d) pumping fluid from the chamber through a pump cavity 104, to a heat exchange catheter 160, through an external heat exchanger 20 which is positioned in heat transfer relationship with a heat generating or removing unit, and pumping the fluid and air displaced by the circulating fluid from the external heat exchanger 20 to the heat exchange fluid reservoir 358; (e) venting the air displaced by the circulating heat exchange fluid from the heat exchange fluid reservoir; (f) repeating steps (a) through (e) for the duration of operation of the catheter.

More particularly, the embodiment of FIGS. 6 and 6A provides the mechanism for passively priming the system with heat exchange fluid from an external source 15. The external fluid source is placed above the reservoir, and is connected by a fluid providing line 16 to the reservoir. The reservoir 358 has a fill port 318 from the fluid providing line 16. Initially, with the catheter out of the patient's body, the pump is operated to draw heat transfer fluid from the external fluid supply and circulate it through the system. The air that is in the system is vented through the hydrophobic air vents. When the pressure in the system is equal to the head pressure from the external fluid source (this will happen at a level which depends on the pump pressure and the height of the external fluid source above the reservoir) the system will essentially be in equilibrium and will cease drawing fluid from the external source. At this point the catheter and cassette system will be considered to be primed. The heat exchange catheter will generally thereafter be inserted into the patient, and as the system is operated, any fluid required to be added to the system to maintain the pressure equilibrium mentioned above will be drawn from the external source which is in fluid communication with the reservoir through fluid providing line. Likewise, any buildup of pressure in the system due, for example to the heating and expanding of the system, will be relieved by fluid flowing back into the external fluid supply source 15. Because of the ability of the system to react to minor expansions and contractions of fluid supply, there is no need to monitor the high level of fluid, and only redundant sensors of the low level need be incorporated into the cassette.

Referring now to the bulkhead embodiment of FIG. 5A and the flow diagram of FIG. 19B, a method for supplying heat exchange fluid to an intravascular heat exchange catheter comprises the steps of: (a) automatically operating a valve to open a fluid pathway between an external fluid source 15 and a chamber 90 in the feedblock section of a bulkhead; (b) transferring fluid from an external fluid source 15 to chamber 90; (c) operating pump head 140 to pump fluid from the chamber 90 into a pump cavity 104, through heat exchange catheter 160, through external heat exchanger 20 which is positioned in heat transfer relationship with a heat generating or removing unit and to exchange fluid reservoir 58; (c) venting all air displaced by the heat exchange fluid supplied to and circulated through the system; (d) continuing steps (a) through (c) until the fluid reservoir is full and excess air is purged from the system; (e) when the fluid reservoir is full, automatically operating a valve to close fluid communication between an external fluid source 15 and chamber 90; (f) continuing steps (b) and (c) for the duration of operation of the catheter. More particularly, the embodiment of FIG. 5A, with its feedblock, provides the mechanism for automatically commencing and ceasing priming the system with heat exchange fluid from an external source 15 and for circulating fluid to the catheter 160 in a closed circuit. The external fluid source 15 has a fluid providing line 16, and the catheter has a fluid supply line 150 and a fluid return line 158. The external heat exchanger 20 has an inlet orifice 36 and an outlet orifice 38. A heat exchange fluid reservoir 58 is connected to the external heat exchanger outlet 38. Pump 140 is positioned in a pump cavity 104, which is connected to fluid supply line 150. A chamber 90 comprises a valve 84, a fill port 18 from the fluid providing line 16, a fluid inlet 87 from the heat exchange fluid reservoir 58, and a fluid outlet 93 to the pump 140. The valve has a first position (FIG. 1B) whereby the fill port 18 from the fluid providing line 16 is open and the fluid inlet 87 from the heat exchange fluid reservoir 58 is closed, and a second position (FIG. 11A) whereby the fill port 18 from the fluid providing line 16 is closed and the fluid inlet 87 from the heat exchange fluid reservoir 58 is open. An optical fluid level detector detects when the heat exchange fluid reservoir 58 is filled to capacity. When the reservoir is not filled to capacity the valve is in its first position. When the reservoir is filled to capacity, the optical fluid level detector operates to move the valve to its second position.

As can be seen from FIG. 19C, the direction of the fluid flow and the inclusion of many of the above described elements are optional, and may be changed, omitted or substituted as is appropriate for the fluid supply system desired. Any such changes, substitutions or omissions may be made without departing from the invention as disclosed, which invention is circumscribed only as is established in the claims.

Referring to FIGS. 11A and 1B, the priming valve 84 is positioned within a central chamber 90, which has two inflow channels, an inflow channel 86 from the fluid reservoir 58 and a filling channel 88 from inlet port 18 from the external fluid source 15. The central chamber 90 also has a outflow channel 92 leading to the pump section. A filter (not shown) may be located between the reservoir and the central chamber to catch any particulate matter that may be in the heat exchange fluid. The chamber is fitted with a guide disc 171 to support the priming valve. The priming valve is operable to fill the closed fluid circuit comprising the heat exchange catheter 160, the external heat exchanger 20 and the bulkhead 30. It may be configured to automatically prime the system.

The embodiment of the priming valve illustrated in FIGS. 11A and 11B is a spool valve 84, which is comprised of a spool valve stem 94, a compressible spring 99 contained within a solid block 101, and a plurality of O-rings 91. The spool valve is operable between a first position (FIG. 11B) and a second position (FIG. 11A), and is controlled by a spool valve activation system 164 which is mounted on the reusable master control unit 186, as shown in FIG. 2. The spool valve activation system 164 comprises a flexible membrane 96, a push rod 98 and a linear actuator 102. The valve stem 94 is located so that its top end is positioned immediately below the membrane 96, which can be a silicon membrane reinforced by cloth which is deformable by a sufficient degree to allow the valve stem to be depressed to travel between the two positions illustrated in FIGS. 11A and 11B. A push rod 98 may depress the valve stem 94 by pushing against the membrane 96 and thence against the top end of the valve stem to operate the valve. The push rod, not contained in the cassette of this invention, may be manually triggered, or may be automatically controlled. The push rod 98 may act, for example by means of a linear actuator 102, which will serve to exert downward pressure on the push rod, as in FIG. 11B or will be in a released position, as in FIG. 11A such that no downward pressure is exerted on the spool valve stem 94.

The invention also encompasses a method for automatically commencing and ceasing the printing of a heat exchange fluid supply system for supplying a heat exchange fluid from an external fluid source 15 to an intravascular heat exchange catheter 160, using the means described above. This method comprises the steps of: (a) first providing power to operate the pump, wherein the reservoir is not filled to capacity and the valve is in its first position and the pump 140 operates to pump fluid: (i) from the external fluid source 15 through the fluid providing line 16 into the fill port 18 of the chamber 90 and out of the fluid outlet 93 into the pump cavity 104; (ii) from the pump cavity 104 to said fluid return line 158 to the catheter 160; (iii) from the catheter 160 through the fluid supply line 150 to the external heat exchanger inlet orifice 36; (iv) from the external heat exchanger outlet orifice 38 to the heat exchange fluid reservoir 58; and (v) into the heat exchange fluid reservoir 58 to fill the reservoir; (b) then filling the reservoir to capacity; at which point (c) the optical fluid level detector operates to move the valve to its second-position and the pump 140 operates to pump fluid from the heat exchange fluid reservoir 58 to the fluid inlet 87 of the chamber 90 and out of the fluid outlet 93 into the pump cavity 104.

When the disposable cassette of the invention is first put into operation, the cassette 10 is initially filled with heat exchange fluid and an external fluid source such as an IV bag of saline is attached to the filling channel 88. In addition, the linear actuator 102 is activated, and the spool valve stem 94 is in its first position (FIG. 11B, the valve stem depressed and the valve in the auto-prep position), depressed sufficiently to allow fluid to flow from the IV bag into the central chamber 90. In particular, the filling channel 88 is open to the outflow channel 92 and the inflow channel 86 is closed, which allows the heat exchange fluid to flow from the external fluid supply source 15 into the chamber 90 and then onto the pump section 100.

When the pump head 140 is active, heat exchange fluid is initially pumped from the external fluid source 15 in to the chamber 90, then through the catheter 160, returning to the bulkhead 30 and then onto the external heat exchanger 20, and from there into the reservoir 58, as would be the case where the system was initially primed. As part of this process, air is expelled through the hydrophobic vents and the reservoir begins to fill with heat exchange fluid. The fluid level in the reservoir rises since fluid is unable to move through outlet channel 62 and inflow channel 86, which is closed due to the position of the spool valve.

The reservoir section is provided with a means to detect when the fluid reservoir is full, as described above, whereby signals are provided to the reusable master control unit that represent or correspond to the level of the heat exchange fluid in the reservoir. Using the data representing the fluid level, the reusable master control unit adjusts the linear actuator so that the position of the spool valve changes and the fluid flow path is altered. Thus when the fluid level in the reservoir 58 rises to a sufficient level, a signal is sent to the reusable master control unit to deactivate the linear actuator 102 so that it moves to a released position and thus withdrawing the push rod 98, resulting in the spool valve stem 94 being in its second position (FIG. 1A, the valve stem relaxed and the valve in the normal operating position). In this second position, the inflow channel 86 is open to the outflow channel 92 and the filling channel 88 to the external fluid source is closed. Thus, fluid from the now full reservoir is directed from inflow channel 86 to outflow channel 92 and then onto the pump section, while fluid flow from the external fluid source is diminished or ceases entirely.

The valve is biased into the up position, that is the position that seals the filling channel 88, and opens the inflow channel 86. In a preferred embodiment the pump would continue to run for a period of time after the level sensor indicated that the system was full to ensure that any air bubbles in the catheter or the external heat exchanger or the bulkhead would be expelled into the reservoir 58 where they could vent to the atmosphere. Since the fluid is being drawn from the bottom of the reservoir through reservoir outlet channel 62, and air moves up towards the top of the reservoir where the hydrophobic vents are located, this acts to purge air from the system. Therefore, it is important to realize that the spool valve may also have a third position that is an intermediate position from its first and second positions described above. In this manner, heat exchange fluid may enter the central chamber 90 from either the reservoir or the external fluid source, or both simultaneously if the valve stem 94 is opened to this intermediate position. So, for example, in an embodiment of the intention that utilizes the pump in a first, intermediate and then second position, fluid would enter the pump solely from the external fluid source 15 (first position, FIG. 11B), then fluid would enter the pump in part from the external fluid source 15 and in part from the reservoir 58 (intermediate position) and finally fluid would enter the pump solely from the reservoir 58 (second position, FIG. 11A).

The method for automatically commencing and ceasing the priming can further comprises continuously supplying the heat exchange fluid from the pump to the catheter 160, by repeating steps (a)(ii) to (a)(v) and step (c)(i) for the duration of operation of the catheter, which can be to 72 hours.

The pump section is readily adapted for use with the reservoir section 40 and feedblock section 80 of the cassette of FIG. 3 or the reservoir section 340 of the cassette of FIG. 4 and is configured to allow for pumping of heat exchange fluid at a constant pressure. In this embodiment of the invention, the pumping mechanism creates rapid flow in a heat exchange fluid supply system for supplying a heat exchange fluid to an intravascular heat exchange catheter, and comprises a cavity having a quasi-cardioid shape, an inlet to the cavity, an outlet from the cavity, a pump head comprising a rotor having a central groove, and a vane slidably mounted in the groove and impinging on the edge of the cavity.

This is illustrated in FIGS. 9 and 12A, where the pump section 100 contains a cavity 104 of quasi-cardioid shape and the pump head 140. The pump head has a rotor 106 which is circular and rotates within the cavity 104, and has a central groove 108 across the entire center of the rotor. A vane 110 is slidably mounted in the groove and impinges on the edge of the cavity 104. As the rotor 106 rotates around its center, the vane 110 moves freely, sliding back and forth within the groove 108, with the ends of the vane 120, 122 being continuously in contact with the edge of the cavity 104.

A fluid inlet channel 112 leads from the feedblock section 80 and opens into the cavity 104 just beyond the edge of the rotor 106. A fluid outlet channel 114 opens into the cavity 104 on the opposite side of the rotor 106 and leads to the feedblock section 80. As the rotor 106 rotates, the vane 120 is in continuous contact with the cavity wall 123 in relatively fluid tight, contact. Fluid enters into the cavity 104 from the inlet channel 112 and is contained in the cavity between the cavity wall 123, the rotor wall 124 and the vane 110. As the rotor 106 rotates the vane also moves. This causes the fluid path to increase in area as it is filled with heat exchange fluid from the inlet channel 112, and then decrease in area as the vane pushes the heat exchange fluid through outlet channel 114. The rotor wall 124 is in relatively fluid tight contact with the wall of the cavity along arc 116 and therefore fluid cannot travel directly from the inlet channel 112 to the outlet channel 114 of the pump. As the rotor rotates, fluid is pumped from the inlet channel 112 around the quasi-cardioid shaped cavity and pushed by the vane out the outlet channel 114. The configuration of the fluid path can be likened to a "crescent" shape, as can be seen in FIG. 12A.

The pump is designed to rotate within the range of 200-1000 rpm and to function for up to 72 hours. The choice of materials should be selected to accommodate these needs, and suitable materials are described below. It is an additional advantage of the curved edges 120 and 122 on the vane that the point of contact between the vane edges and the cavity wall 123 changes constantly through the rotation of the rotor and thus avoids a single wear point on the edges of the vane.

This allows the vane to rub against the wall of the cavity for as long as 72 hours and yet retain a relatively fluid tight contact between the edges of the vane and the wall of the cavity. In a preferred embodiment, the vane is designed to fit in the cavity 104 at room temperature with a slight clearance, for example 0.005 inches. This clearance is one means of accommodating the transient and steady state thermal changes that occur during operation and allows for expansion of the vane due to an increase in temperature during operation. In this manner; at the temperatures that are encountered during normal operation, the ends of the vane 120, 122 will maintain adequate contact with the wall 123 of the cavity 104 for pumping.

There are numerous other vane designs that also accommodate thermal changes so that the vane remains in continuous contact with the wall of the cavity and is able to move smoothly within the cavity. FIGS. 20A, 20B and 20C are side views of examples of such designs. In FIG. 20A, the vane 181 is configured with cut-out sections 173, 175, which allow for expansion or contraction of the vane during operation. In FIG. 20B, the vane 182 is configured with a center section 177 made of a compressible material to accommodate expansion or contraction of the end portions 179 during operation. In FIG. 20C, the vane 183 is configured with a center spring 211 to bias the end portions 209 outward during operation to contact the wall of the cavity regardless of the temperature of the vane.

One embodiment of the invention relates to the geometry of the quasi-cardioid shaped cavity 104 having a circumference and an inlet 112 and an outlet 114 thereto, that is part of the pumping mechanism of the disposable cassette 10, which cassette is also comprised of a pump head 140 comprising a rotor 106 having a central groove 108 and a diameter "D", and a vane 110 having length "L" slidably mounted in the groove and impinging on the edge of the cavity. As shown in FIG. 12B, the circumference of the cavity has four arcs, where the radius "R" or each arc has its center at the center of the rotor 106 and is measured to the cavity wall 123.

The four arcs 116, 117, 118 and 119 are as follows: (a) a first arc defined as 330° to 30° and having a radius $R_1$, (b) a second arc defined as 150° to 210° and having a radius $R_2$, (b) a third arc defined as 30° to 150° and having a radius $R_3$, and (d) a fourth arc defined as 210° to 330° and having a radius $R_4$. These measurements are based upon the center of the rotor and 0° is identified with the point midway between the inlet and the outlet of the cavity, i.e., the line projected from the center of the rotor 106 and the point on the cavity wall that is midway between the inlet channel 112 and the outlet channel 114 is designated as the base line, from which 0-360° angles are measured, in a clockwise fashion. The four radii are defined as follows:

$$R_1 = D/2$$
$$R_2 = L - (D/2)$$
$$R_3 = (D/2) + \{[(L-D)/2] \cdot [\cos(1.5\theta + 135)]\}$$
$$R_4 = (D/2) + \{[(L-D)/2] \cdot [\cos(1.5\theta - 315)]\}$$

Therefore, arc 116 (330° to 30°) is circular and thus has a constant radius, designated $R_1$; arc 117 (30° to 150°) is not circular since its radius changes as the angle of rotation (designated "θ") increases from 30° to 150°, and is designated $R_3$; arc 118 (150° to 210°) is also circular and thus also has a constant radius, designated $R_2$; and arc 119 (210° to 330°) is not circular since its radius changes as the angle of rotation decreases from 210° to 330°, and is designated $R_4$. These calculations are somewhat approximate because the vane has width, and the end of the vane also has a radius (i.e. is curved) and the exact contact point between the vane and the wall of the cavity varies slightly with the rotation of the rotor. Since both ends of the vane have the same radius of curvature, this is equal on each side, and the exact shape of the cardioid cavity can be adjusted to compensate for this slight variance and still maintain contact at all points between the vane and the cavity wall.

Turning to FIG. 13, the rotor 106 of the pump head is made of a rigid and durable material with adequate lubricity to sustain a long period of close contact with the cavity wall 123 while rotating without undue wear. The rotor 106 may be made of, for example, polyvinylidene fluoride, and the vane 120 may be made of a material such as high density polyethylene. The rotor is mounted on a shaft 128 by means of a pin 129 and has a seal 130 and a bearing 132 separated by an optional spacer 131, provided in a manner known to those of skill in the art of rotating shafts mounted in fluid-tight arrangement.

The shaft 128 protrudes below the rotor 106 and is fitted with three wheels 134, 136 and 138 which cooperate with a pump drive mechanism 184 housed in the reusable master control unit 186, which imparts rotational motion to the shaft and thence to the rotor. The top most wheel 134 is a smooth alignment wheel, the middle wheel 136 is a toothed drive wheel, and the bottom most wheel 138 is another smooth alignment wheel. The drive wheel 136 can be constructed, for example, of a plastic material such as nylon or polyurethane. The alignment wheels 134 and 138 can be constructed, for example, of a polycarbonate material. These three wheels cooperate with a plurality of wheels on the reusable master control unit 186, two of which are depicted in FIG. 2 as guide wheels 190 and 192. A toothed motor wheel 188 is driven by the pump drive mechanism 184, and is shown in FIGS. 14 and 15, which depict placement of the pump wheels 134, 136 and 138 within the control unit 186. FIGS. 2 and 14 also shows placement of the gear shield 19, which covers the opening in the control unit 186 once the cassette 10 is positioned in place.

When the cassette 10 is inserted into the reusable master control unit 186, the toothed drive wheel 136 engages the toothed portion 189 of motor wheel 188. The drive wheel 136 and motor wheel 188 are held in snug juxtaposition by contact between guide wheels 190, 192 and alignment wheels 134, 138, respectively. As can be seen in FIG. 15, the guide wheels have a larger diameter top 191 and bottom 193 section, with a small diameter middle section 195. This allows the top 191 to fit snugly against alignment wheel 134 and the bottom 193 to fit snugly against alignment wheel 138, while at the same time the middle section 195 will not come in to contact with the toothed drive wheel 136. The guide wheels can be machined as a single spool-shaped unit or the top, middle and bottom sections can be separate pieces that are permanently affixed together. The toothed motor wheel can also be designed to have a slightly larger top section 207 that fits snugly against alignment wheel 134 and/or a slightly larger bottom section 208 that fits snugly against alignment wheel 138. Preferably the motor wheel makes contact with at least one of the smooth alignment wheels.

The positioning of the alignment and guide wheels causes the teeth of motor wheel 188 and drive wheel 136 to engage at the appropriate distance so that the teeth are not forced tightly together. The diameter of the smooth alignment wheels 134, 138 will be approximately the pitch diameter of the drive wheel 136 to provide proper positioning of the drive teeth.

Similarly, the diameter of the top and bottom sections, 207, 208, of the motor wheel 188 will be approximately the pitch diameter of the toothed portion 189 of the motor wheel 188. This is advantageous in imparting smooth rotation motion without imparting side forces to the drive shaft, or causing friction between the teeth by virtue of their being jammed together.

The diametral pitch of the drive wheel 136 and the motor wheel 188 are the same; however they will typically have different diameters. For example, a suitable diametral pitch is 48 (48 teeth per inch in diameter), which has been found to provide adequate strength with minimal noise during operation. A typical drive wheel 136 will have a pitch diameter of 1", while the corresponding motor wheel 189 will have a pitch diameter of about ⅜".

The pump is designed to operate for significant periods of time, for example in excess of 72 hours, at fairly high rotational speeds, for example approximately 800 rpm, and to operate to pump fluids of temperature that vary between approximately 0° C. and 45° C. It is desirable that the heat exchange catheter is supplied with fluid at a relatively constant pressure at the inlet to the catheter, for example about 40-46 psi, but wear and temperature variations may affect the output pressure of the pump. In the embodiment which includes the pressure regulator, the pump is designed to have an output pressure slightly higher than the optimal pressure for the heat exchange catheter, for example 42-48 psi, and the pressure is regulated down to the desirable pressure of 40-46 psi. If the output pressure of the pump varies, the pressure regulator can be incorporated into the disposable heat exchange supply cassette 10 to ensure that the heat exchange catheter is provided heat transfer fluid at a relatively constant pressure. The pressure regulator can be, for example, a pressure regulator valve or a pressure damper used with a constant current supply in the disposable heat exchange supply cassette 310.

A preferred pressure regulator valve is described here, but it may be readily perceived that one of ordinary skill may substitute any appropriate pressure regulator valve for this function. In the preferred embodiment of the pressure regulator valve shown in FIG. 16, the outlet 114 of the pump is fluidly connected to the inlet of the pressure regulator chamber 198 by means of channel 196. The pressure of the fluid at the pump output may vary somewhat depending on wear and fluid temperature, and may be, for example, 45-54 psi.

A pressure regulator shaft 200 is mounted in the fluid reservoir 58 through the mounting block 75. This may be in the form of a shaft with screw threads mounted in a hole 194 in the block with mating screw threads. A reference spring 202 is mounted between the shaft 200 and a diaphragm 204. The diaphragm may be a membrane, for example, a cloth reinforced silicone membrane. The pressure on the reservoir side of the diaphragm is the pressure of the fluid in the reservoir 58, which by virtue of the hydrophobic gas permeable vents 54 is essentially atmospheric pressure, plus the pressure applied by reference spring 202. The pressure of reference spring 202 may be adjusted by turning the shaft in the hole and thus tightening or loosening the spring against the diaphragm. A pressure block 206 is attached between the diaphragm 204 and the reference screw 202 to apply distribute the pressure of the spring to the reservoir side of diaphragm 204.

On the other side of the diaphragm 204 a push rod 210 is attached. The push rod 210 extends through a throttle chamber 212. The throttle chamber 212 has a cloverleaf cross sectional configuration in the form of a central throttle aperture 216 surrounded by four lobes 214, as may best be seen in FIG. 17. The end of the push rod 210 distal of the diaphragm 204 extends to the end of the throttle chamber 212 to throttle aperture 218. A counter spring block 220 is mounted across the face of the aperture 218 and is biased toward the aperture by means counter spring 222. This counter-spring block 220 may seal down against the open aperture 218 to create a fluid-tight seal between the sensing chamber 224 and the regulator chamber 198. Alternatively, if the pressure applied against the diaphragm by the spring 202 and the pressure in the reservoir 58 is sufficient to deform the diaphragm inward toward the sensing chamber 224, the push rod 210 forces the counter-spring block 220 away from the throttle aperture 218 and thus opens a throttle gap through which fluid may flow between the regulator chamber 198 and the sensing chamber 224. Because the throttle gap is relatively narrow, there is a pressure drop as fluid flows through the throttle gap. In practice, the reference spring 202 is adjusted so that the pressure against the diaphragm 204 and thus against the push rod 210 is about 43 psi. When the pressure in the regulator reservoir 198 is greater than 43 psi, it forces the counter spring block 220 closer to the throttle aperture 218 thus narrowing the throttle gap. This functions to automatically adjust the throttle gap so that the pressure drop across the throttle gap is the same as the excess pressure between the fluid in the regulator reservoir 198 and the pressure set by the reference spring 202 against the diaphragm 204, generally 43 psi. This acts to regulate the pressure of the fluid in the sensing chamber 224 to 43 psi. The fluid exits the sensing chamber through outlet 220 and thence to fluid supply line 150 to the catheter. In this way fluid at a relatively constant pressure is supplied to the catheter. It may also be seen that such a pressure regulator may function to damp any pressure variations, such as vibrations in the fluid line generated by the pump. For such uses, a regulator as described herein may be adequate. Other pressure regulators, as are well known in the art, will also suffice for regulating pressure of the pumped fluid, including systems for controlling other flow characteristics such as dampening vibrations.

In operation, the rotor 106, including vane 110, is rotating at a sufficiently constant rate to generate relatively constant pressure. However, due to the shape of the cavity 104, a variable pressure can be imparted to the fluid being moved by the vane, resulting in pressure fluctuations or uneven fluid flow in the fluid flowing from the feedblock section 80 to the catheter through fluid supply line 150. These pressure fluctuations or uneven fluid flow may cause undesirable vibration of the catheter through which the fluid is flowing. In the embodiment described in FIG. 5, the pressure regulator serves to eliminate undesirable pressure fluctuations.

However, it may be desirable to eliminate the pressure regulator valve, pressure regulator chamber and sensing chamber from the cassette design. In that instance, another means of insuring constant pressure and providing for smooth fluid flow can be incorporated into the cassette design.

The pump drive mechanism 184 typically comprises an electric motor and a power supply that provides the necessary current to run the motor. Constant current can be attained by directing the voltage from the power supply to an amplifier which adjusts and controls the fluctuating voltage input to provide a constant current output to the motor. With a constant current supplied to the electric motor that runs the pump, the motor provides for constant torque to the pump head 140, which ultimately provides for constant pressure supplied to the catheter 160.

Accordingly, in one embodiment of the disposable cassette of the invention, the cassette comprises an external heat exchanger having an inlet and an outlet, a first fluid supply line in fluid communication with the heat exchanger inlet, a disposable pump head having a pump inlet in fluid communication with the heat exchanger outlet and having a pump outlet, a second fluid supply line in fluid communication with the pump outlet for receiving fluid pumped out of the pump outlet, and an optional pressure regulator in fluid communication with the pump outlet for regulating the pressure of fluid pumped from the pump head. The pump head is actuated by an electric motor that is controlled by an amplifier controller, where the amplifier controller supplies a constant current to the pump head thereby causing the pump head to supply a relatively constant pressure to the fluid in the second fluid supply line.

In another embodiment of the invention, the cassette comprises: (a) an external heat exchanger comprising a structural member and a compliant member, where the compliant member is sealed to the structural member in a pattern that forms a flow channel between the compliant member and the structural member, and where the flow channel has an inlet and an outlet; (b) a first fluid supply line in fluid communication with the flow channel inlet; (c) a bulkhead comprising a reservoir and a disposable pump head, where the reservoir contains an inlet in fluid communication with the flow channel outlet, and further has a fluid level detector for detecting the level of fluid within the reservoir, wherein the pump head is a cardioid vane pump head having an inlet and an outlet, and the pump head is actuated by an electric motor, where the pump inlet is in fluid communication with the reservoir outlet and the electric motor is controlled by an amplifier controller, where the amplifier controller supplies a constant current to the pump head thereby causing the pump head to supply a relatively constant pressure to the fluid in the second fluid supply line; (d) a second fluid supply line in fluid communication with the pump outlet for receiving fluid pumped out of the pump outlet; (e) an external fluid source in fluid communication with the reservoir; and (f) a pressure damper in fluid communication with the pump outlet.

One embodiment for providing smooth fluid flow is illustrated in FIG. 18, which is a cross-sectional view of a pressure damper, that may be used in place of the pressure regulator components. In this embodiment of the invention, a pressure damper is included in a heat exchange fluid supply system for supplying a heat exchange fluid to an intravascular heat exchange catheter where the heat exchange fluid supply system has a reservoir section, a feedblock section and a pump section, wherein the pressure damper comprises a pressure dampening chamber filled with a compressible material housed in the feedblock section, adjacent to a flow-through channel having an inlet which leads from the pump and an outlet which leads to the catheter. The compressible material is preferably air tight. Suitable examples include a block of foam, encapsulated foam such as polyethylene foam encased in a polyethylene film, foam enclosed within a sealed plastic pouch, foam coated with or impregnated with plastic or silicone, gas encapsulated within a flexible pouch such as a polyethylene balloon, and so forth.

Referring to FIG. 18, a pressure dampening chamber 230 is positioned adjacent to and in fluid flow communication with the fluid flowing from the pump in the pump outlet channel 314 towards the outlet channel 319. As can be seen in FIG. 18, the dampening chamber need not be positioned directly in the fluid flow path. The chamber must simply be in a position such that it is in contact with fluid being pumped from the pump through channel 314. The chamber 230 is partially filled with a compressible material 232. As fluid contacts the compressible material 232, the material compresses slightly and then returns to its original configuration, and in doing so acts as a cushion to absorb minor pressure fluctuations uneveness of the fluid flow. This compressible material movement thus has the effect of smoothening the fluid flow.

The external heat exchanger 20 is attached to the bulkhead 30 or bulkhead 330 by means of a mechanical seal formed when the external heat exchanger is attached over the bulkhead and a cover plate shown as cover plate 168 in FIG. 3 and as cover plate 368 in FIG. 4. The cover plate is attached over the external heat exchanger and attached to the bulkhead, trapping the extended attachment 48 of the external heat exchanger between the cover plate and the bulkhead. Referring to the embodiment of FIG. 3, the cover plate is formed with a handle 170, a vent aperture 172 that is located over and seal the periphery of the hydrophobic gas permeable vents 54 to allow any air present in the fluid reservoir 58 to vent to the atmosphere. The cover plate is also formed with a priming valve aperture 174 that provides access to the cover of the priming valve 84, for example so that push rod 98 is able to contact the flexible membrane 96 and depress the valve stem 94 during the automatic priming sequence described above. Located on the bottom of the cover plate 168 are two circular recessed areas (not shown), a first recess 178 that fits over and seals the priming valve 84 and a second recess 180, containing an O-ring 182 that fits over and seals cavity 104. The bottom of the cover plate may have one or more straight recessed areas into which a portion of the fluid lines such as lines 16, 150, 158 may be positioned. The cover plate may be secured to the bulkhead by any suitable means, for example by a plurality of suitably positioned hex-headed screws 176.

The cover plate is also configured to have one or more means for indicating to the user that the cassette is in the correct position for operation. For example, the cover plate may have a slot that operates to depress a switch on the control unit to indicate proper placement. Similarly, the cover plate may have slots 199 and 201, with corresponding depressions 203 and 205, which correspond to bearings on the control unit. When the cassette is being positioned within the control unit, the bearings will move along the slots 199 and 201 and once the cassette is completely in place, the bearings will move into depressions 203 and 205, with an audible click to inform the user that placement is complete.

Cover plates 168 and 368 are configured in a similar manner, with the exception that cover plate 368 does not have a priming valve aperture 174 or first recess 178 since the embodiment of FIG. 4 does not have a priming valve.

Referring back to FIGS. 1 and 2, the disposable fluid supply cassette 10 of the invention is shown as being attached to a heat exchange catheter 160, external fluid source 15 and positioned in cooperation with a suitable reusable master control unit 186. Prior to commencing treatment, the cassette is inserted into the reusable master control unit, the external fluid source is attached to the fill port and the pump is automatically or passively primed and filled, after which the catheter is ready for insertion in the vasculature of the patient, for example in the inferior vena cava or the carotid artery. Chilled or warmed biocompatible fluid such as saline, is pumped into the closed circuit catheter, which exchanges heat directly with the patient's blood. The control unit serves to automatically control the patient's temperature. Once treatment with the catheter is complete, the catheter is removed from the patient and the cassette is removed from the reusable master control unit. Both the catheter and cassette are then discarded. The reusable master control unit, however, which never comes into direct contact with the heat exchange fluid, is ready for immediate use for treatment on other patients, along with a new cassette and catheter and fresh external fluid source.

Each of the patents, publications, and other published documents mentioned or referred to in this specification is herein incorporated by reference in its entirety.

While the present invention has been described with reference to the specific embodiments thereof, it should be understood by those skilled in the art that various changes may be made and equivalents may be substituted without departing from the scope of the invention. In addition, many modifications may be made to adapt a particular situation, material, composition of matter, process, process step or steps, while remaining within the scope of the present invention. Accordingly, the scope of the invention should therefore be determined with reference to the appended claims, along with the fill range of equivalents to which those claims are entitled.

What is claimed is:

1. A method for providing a temperature regulated source of heat exchange fluid for heat exchange catheters, comprising the steps of:
    providing a disposable circuit assembly comprising an external heat exchanger, a heat exchange catheter, and a housing defining a pump section and a reservoir section, the housing having an air vent disposed in a wall of the housing defining the reservoir section, the pump section including a pump head, said external heat exchanger, pump head and reservoir and heat exchange catheter in fluid communication such that fluid pumped by the pump head of the bulkhead is circulated through said heat exchange catheter and said external heat exchanger, and said air vent allows passage of gas in and out of said disposable circuit assembly through said vent but does not allow passage of liquid in and out of said disposable circuit assembly through said air vent;
    providing a heat generating or removing unit in heat exchange relationship with said external heat exchanger;
    providing an external fluid source in fluid communication with said disposable circuit assembly;
    providing a valve between said external fluid source and said disposable circuit assembly, said valve having an open position which permits the flow of heat exchange fluid from said external fluid source into said disposable circuit assembly and a closed position which prevents the flow of heat exchange fluid from said external fluid source to said disposable circuit assembly;
    providing a level sensor within said disposable circuit assembly to sense when the fluid level in said disposable circuit assembly is full, said level sensor generating a signal in response to said full fluid level;
    initially maintaining said valve in said open position until said sensor senses that the fluid level in said disposable circuit assembly is at an adequately full level; and
    operating said valve into said closed position in response to said signal;
    circulating heat exchange fluid from said external source through said disposable circuit assembly by means of pumping with said pump head while simultaneously venting any gas contained in said disposable circuit assembly out through said air vent; and
    controlling the temperature of said heat exchanger fluid in said disposable circuit assembly by controlling the temperature of said heat generating or removing unit.

2. The method of claim 1 further comprising the step of controlling the pressure of said fluid as said fluid is circulated through said disposable circuit assembly.

3. The method of claim 2 wherein said pressure control comprises a pressure regulator in fluid communication with said disposable circuit assembly.

4. The method of claim 3 wherein said pressure regulator is a pressure damping mechanism.

5. The method of claim 2 wherein said pump head is operated by an electric motor, and said pressure is controlled by maintaining a predetermined current to said electric motor.

* * * * *

UNITED STATES PATENT AND TRADEMARK OFFICE
CERTIFICATE OF CORRECTION

PATENT NO.        : 7,658,755 B2                                              Page 1 of 2
APPLICATION NO.   : 10/627487
DATED             : February 9, 2010
INVENTOR(S)       : Timothy R. Machold et al.

It is certified that error appears in the above-identified patent and that said Letters Patent is hereby corrected as shown below:

Title page item (*) Notice: should read as follows:   Subject to any disclaimer, the term of this patent is extended or adjusted under 35 U.S.C. 154(b) by 1306 days.

Column 5, line 7, after "rotor" delete "is".

Column 5, line 9, after "outlet" insert --,--.

Column 5, line 59, delete "though" and insert instead --through--.

Column 5, line 59, before "vents" insert --air--.

Column 10, line 15, delete "any".

Column 10, line 28, after "inlet" insert --is--.

Column 14, line 42, delete "component" and insert instead --components--.

Column 18, line 1, delete "position" and insert instead --positioned--.

Column 18, line 5, delete "even" and insert instead --event--.

Column 18, line 40, after "such" insert --a--.

Column 19, line 21, after "enter" insert --the--.

Column 19, line 46, delete "though" and insert instead --through--.

Column 20, line 31, delete "a" and insert instead --an--.

Column 21, line 67, delete "1B" and insert instead --11B--.

Signed and Sealed this

Twenty-fourth Day of August, 2010

David J. Kappos
*Director of the United States Patent and Trademark Office*

Column 23, line 46, delete "1A" and insert instead --11A--.

Column 27, line 60, delete "distribute".

Column 28, line 5, after "means" insert --of a--.

Column 30, line 1, after "fluctuations" insert --and--.